(12) United States Patent
Hattori et al.

(10) Patent No.: US 7,109,232 B2
(45) Date of Patent: Sep. 19, 2006

(54) **COMPOUNDS FROM *ANTRODIA CAMPHORATA* HAVING ANTI-INFLAMMATORY AND ANTI-TUMOR ACTIVITY**

(75) Inventors: Masao Hattori, Toyama (JP); Chia-Chin Sheu, Kuei Shan Hsiang (TW)

(73) Assignee: Simpson Biotech Co., Ltd., (TW)

( * ) Notice: Subject to any disclaimer, the term of this patent is extended or adjusted under 35 U.S.C. 154(b) by 0 days.

(21) Appl. No.: 10/793,820

(22) Filed: Mar. 8, 2004

(65) Prior Publication Data

US 2005/0197384 A1    Sep. 8, 2005

(51) Int. Cl.
*C07D 207/267* (2006.01)
*C07D 207/46* (2006.01)
*A61K 31/4015* (2006.01)

(52) U.S. Cl. .................. 514/425; 548/542; 548/548

(58) Field of Classification Search ............... 548/542, 548/545, 548; 514/423
See application file for complete search history.

(56) References Cited

U.S. PATENT DOCUMENTS

| 4,188,398 A | | 2/1980 | Mndzhoian et al. | |
|---|---|---|---|---|
| 4,431,661 A | * | 2/1984 | McKenzie et al. | ........... 424/274 |
| 4,544,665 A | * | 10/1985 | Epstein et al. | ............... 514/412 |
| 2003/0113297 A1 | | 6/2003 | Chen et al. | |
| 2003/0148517 A1 | | 8/2003 | Chen et al. | |
| 2004/0092000 A1 | | 5/2004 | Wu et al. | |

FOREIGN PATENT DOCUMENTS

GB      1 560 464       2/1980

OTHER PUBLICATIONS

Nakamura, Norio; et al, Five New Maleic and Succinic Acid Derivatives from the Mycelium of *Antrodia camphorata* and their Cytotoxic Effects on LLC Tumor Cell Line, 2004, J. Nat. Prod., 67, 46-48.*
Crider et al. "Synthesis of cis-4-methyl-3-phenylphyrrolidines as Potential Dopaminergic Agonists," J. Heterocyclic Chem., 25(5), pp. 1407-1412 (1988).*
Tschappat, K., Journal of Heterocyclic Chemistry, vol. 24, No. 3, pp. 673-676, 1987.*
Nakamura, Norio et al., Five New Maleic and Succinic Acid Derivatives from the Mycelium of *Antrodia camphorate* and Their Cytoxic Effects on LLC Tumor Cell Lines, J. Nat. Prod. (2004), vol. 67, pp. 46-48, XP-002316113.
Tominaga, Yoshinori, Synthesis of Methylthiomaleimides for the Preparation of Pyridazines and Related Compounds, Journal of Heterocyclic Chemistry, vol. 39, No. 3, (2002) pp. 571-591, XP-002316114.
Wijnberg, et al., A Regioselective Reduction of *GEM*-Disubstituted Succinimides, Tetrahedron, vol. 34, No. 2, (1978) pp. 179-187, XP-002316115.
Mau, Jen-Leun, Antioxidant properties of methanolic extracts from two kinds of *Antrodia camphorate* mycelia, Food Chemistry, vol. 86, Jun. 2004, pp. 25-31, XP002316116.
Dai, Yu-Yun et al., The Protection of *Anthrodia camphorate* against Acute Hepatotoxicity of Alcohol in Rats, Journal of Food and Drug Analysis, vol. 11, No. 3 (2003), pp. 177-185, XP-002316117.
You-Cheng Hseu et al., Protection of oxidative damage by aqueous extract from *Antrodia camphorate* mycelia in normal human erythrocytes, Life Sciences, vol. 71, (2002), pp. 469-482, XP-002315118.
European Search Report, dated 2 Feb. 2, 2005, for Application No. EP 04 25 4939.

* cited by examiner

*Primary Examiner*—Kamal A. Saeed
*Assistant Examiner*—Nyeemah Grazier
(74) *Attorney, Agent, or Firm*—Harness, Dickey & Pierce

(57) ABSTRACT

The present invention relates to novel mixture and maleic and succinic acid derivatives from mycelium of *Antrodia Camphorata* and the medical use thereof. The present invention relates to the composition or mycelium comprising the compounds of the invention.

12 Claims, 13 Drawing Sheets

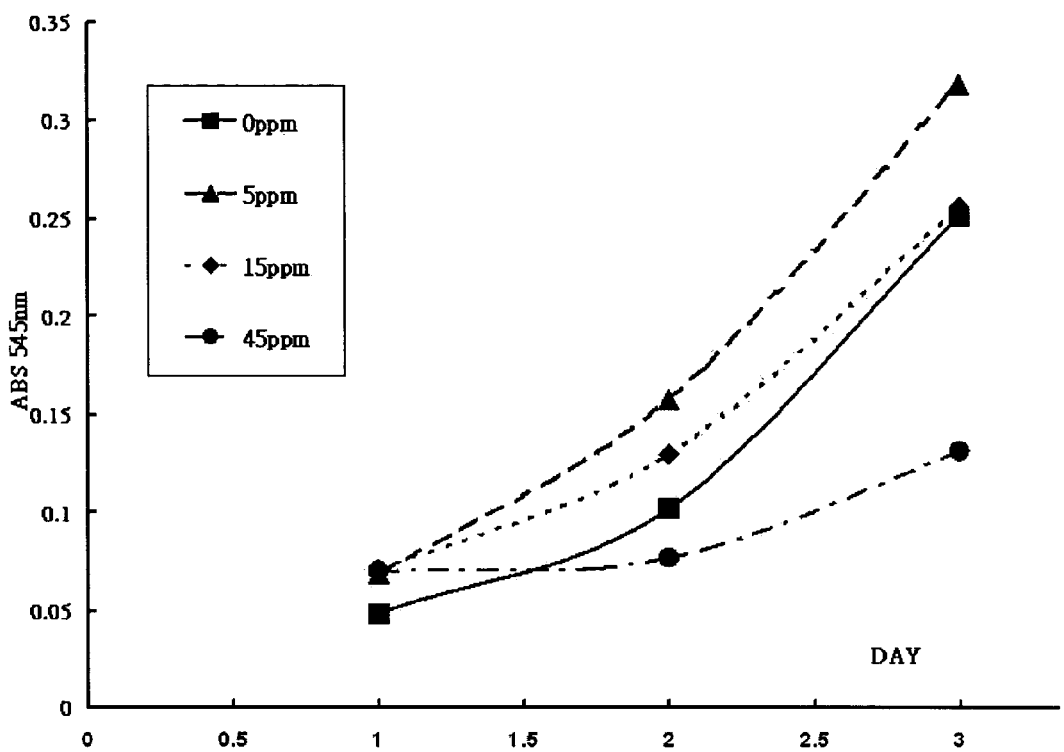
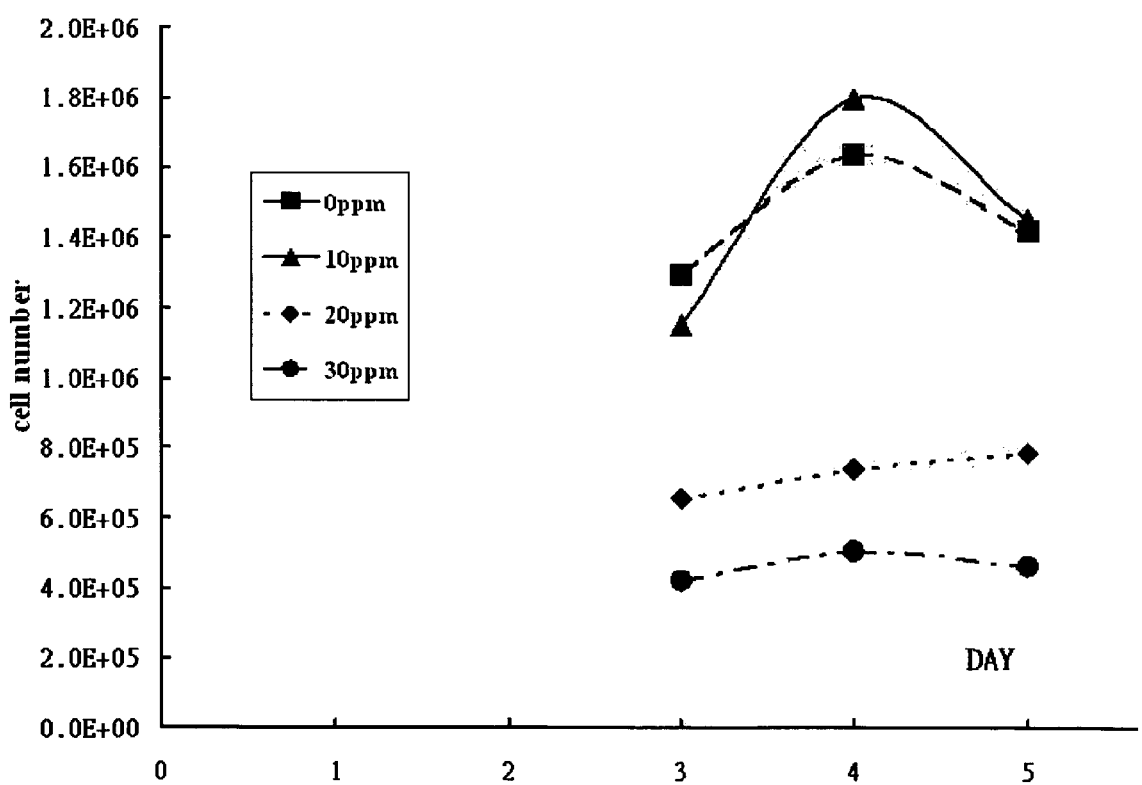
Figure 4-a (upper) and Figure 4-b (down)

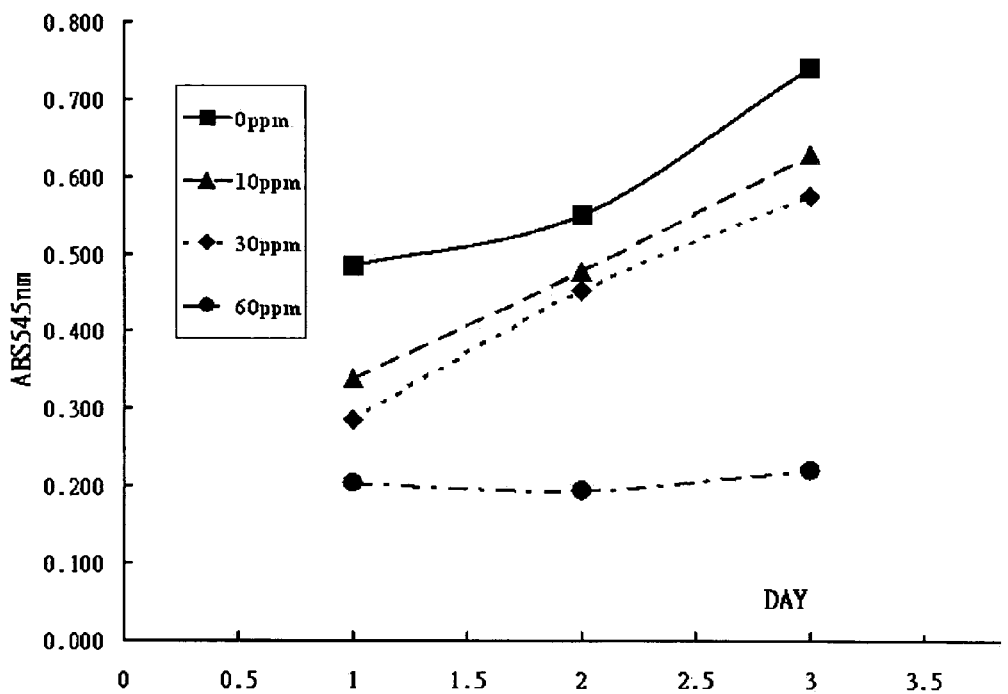
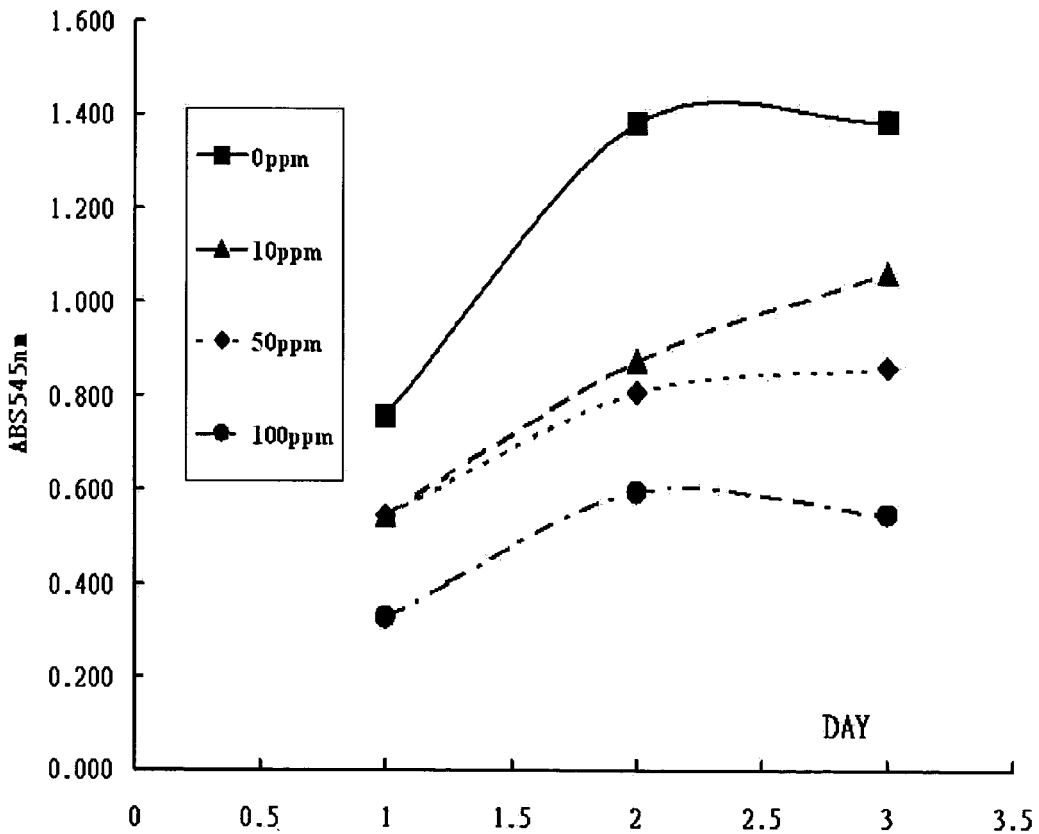
Figure 4-c (upper) and Figure 4-d (down)

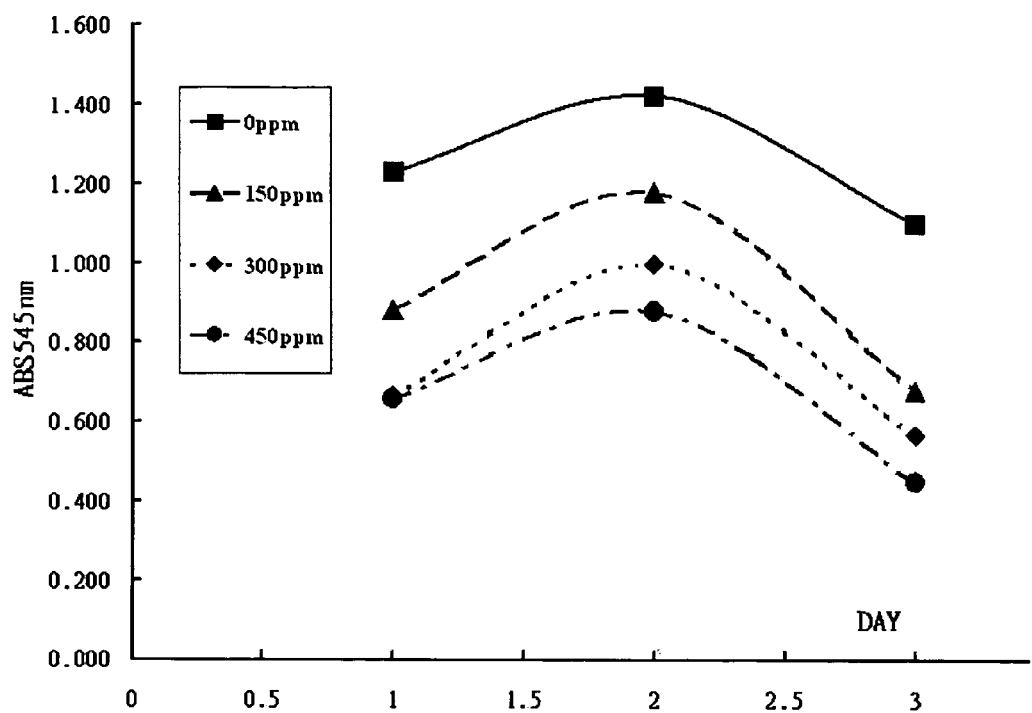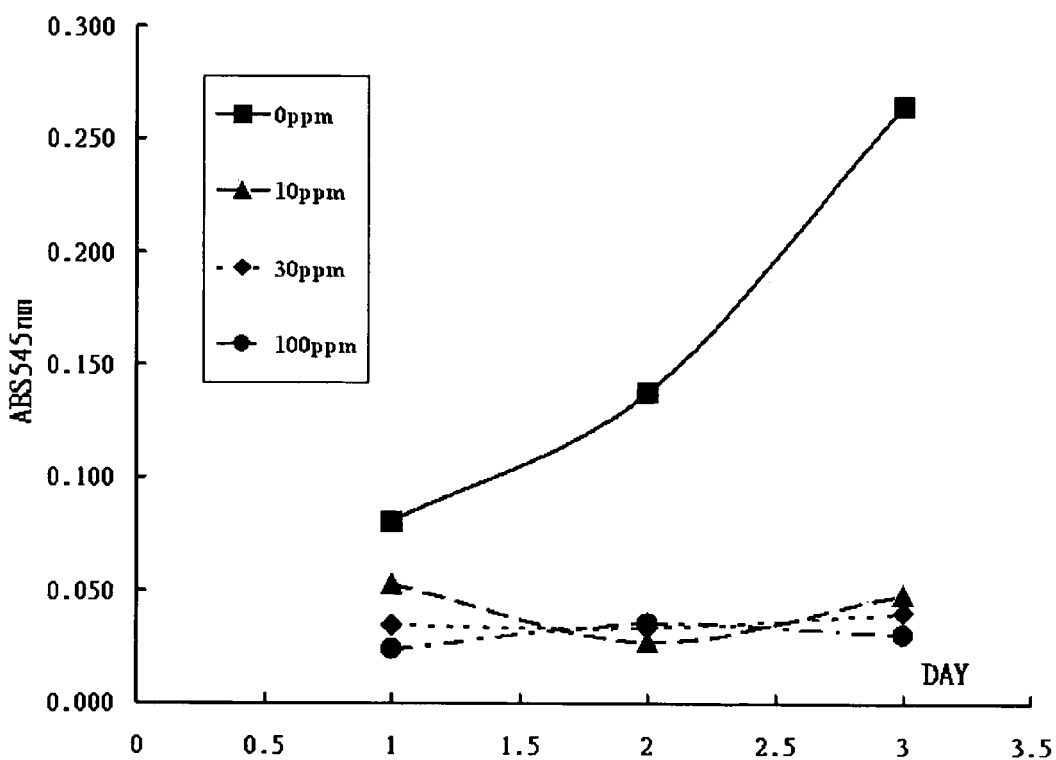
Figure 5-a (upper) and Figure 5-b (down)

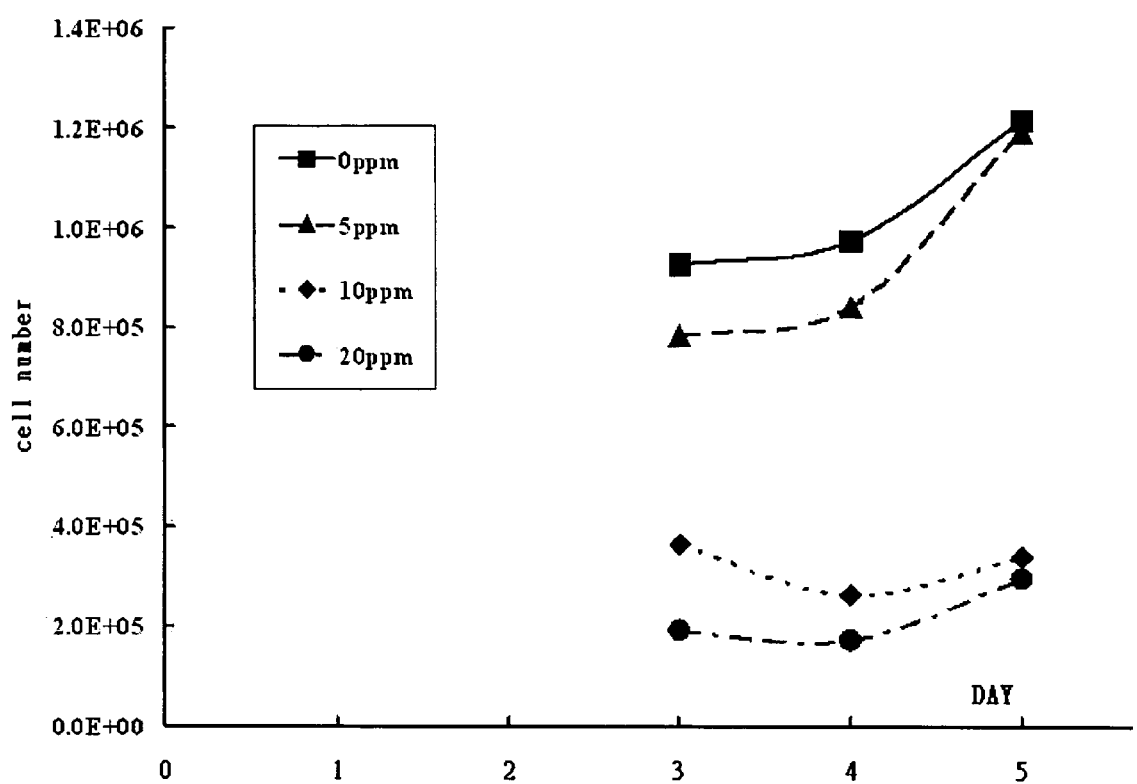
Figure 5-c

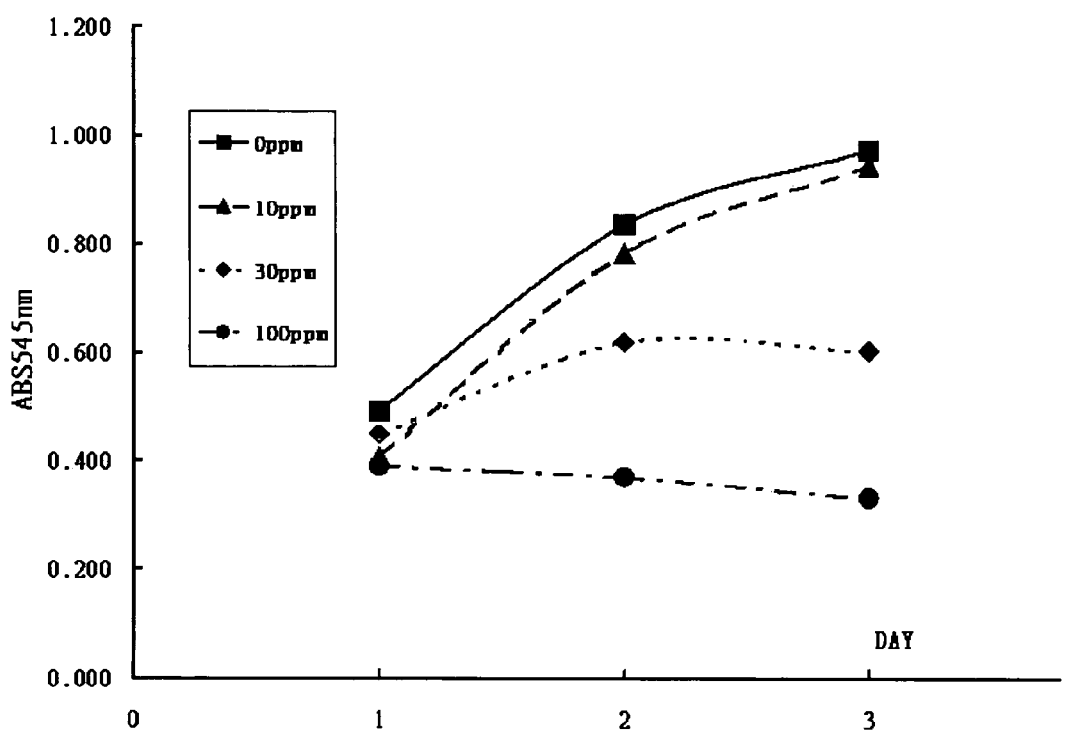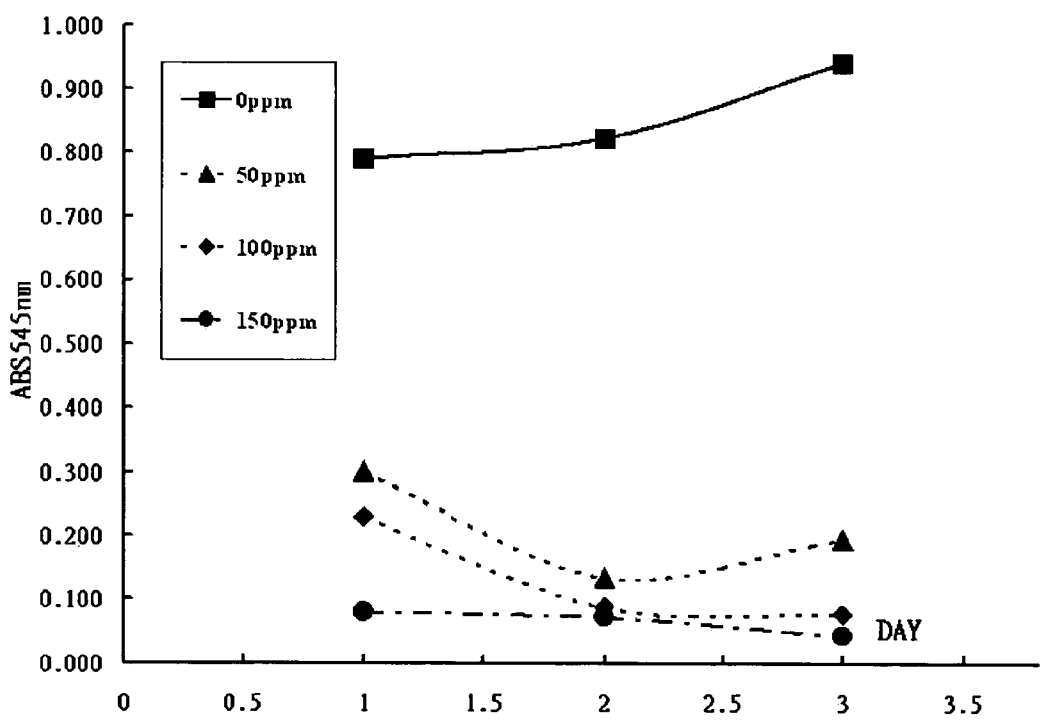
Figure 6-a (upper) and Figure 6-b (down)

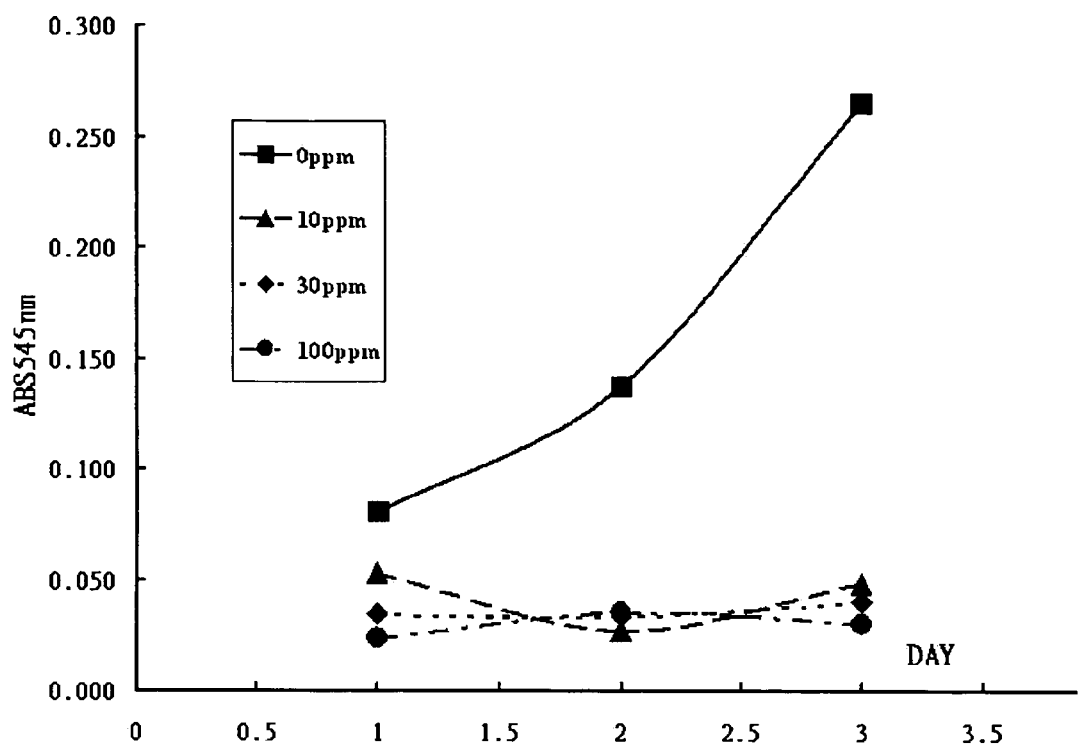
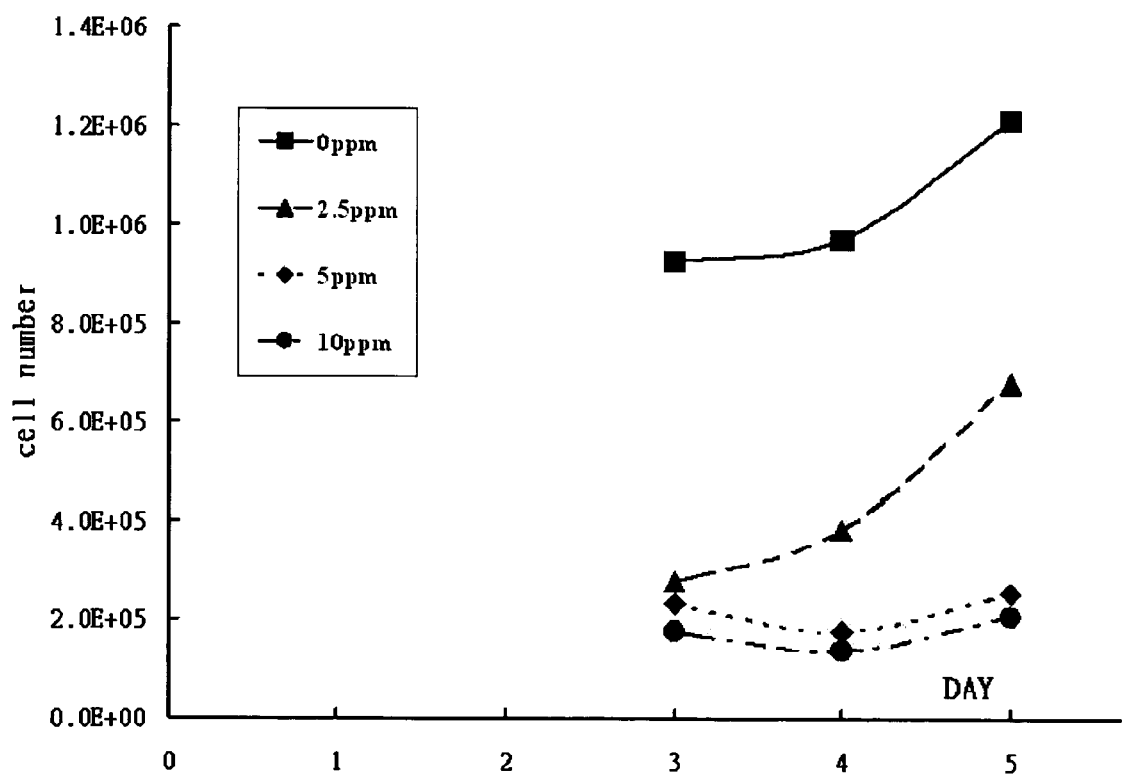
Figure 6-c (upper) and Figure 6-d (down)

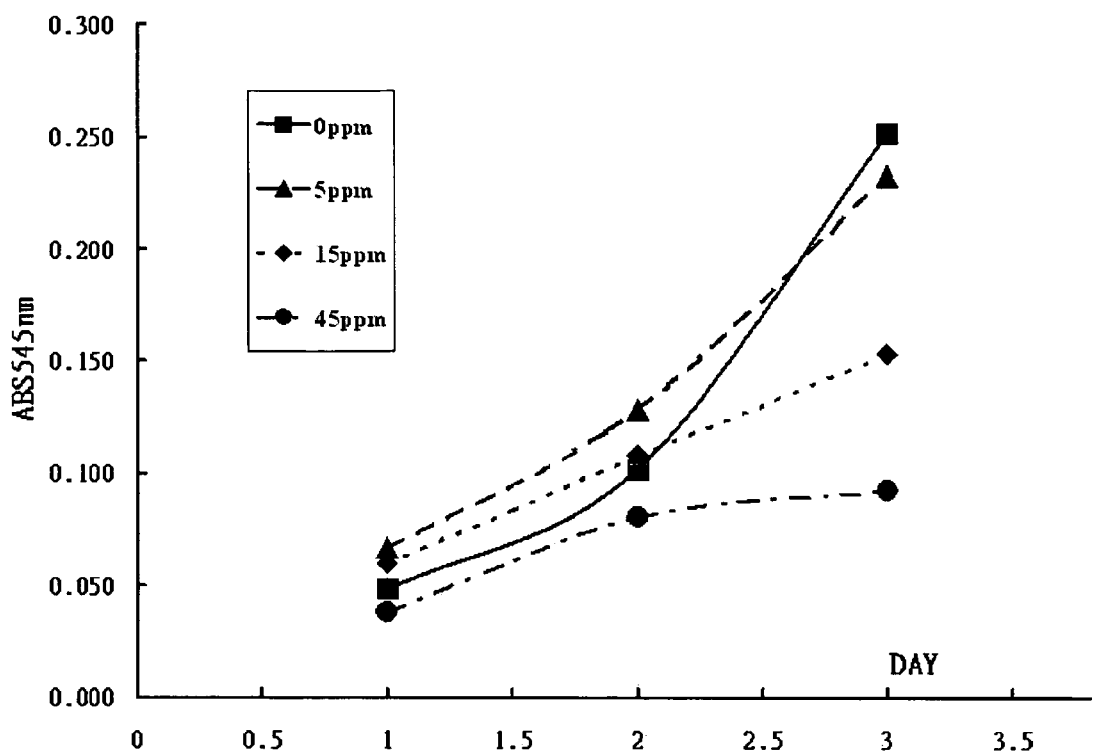
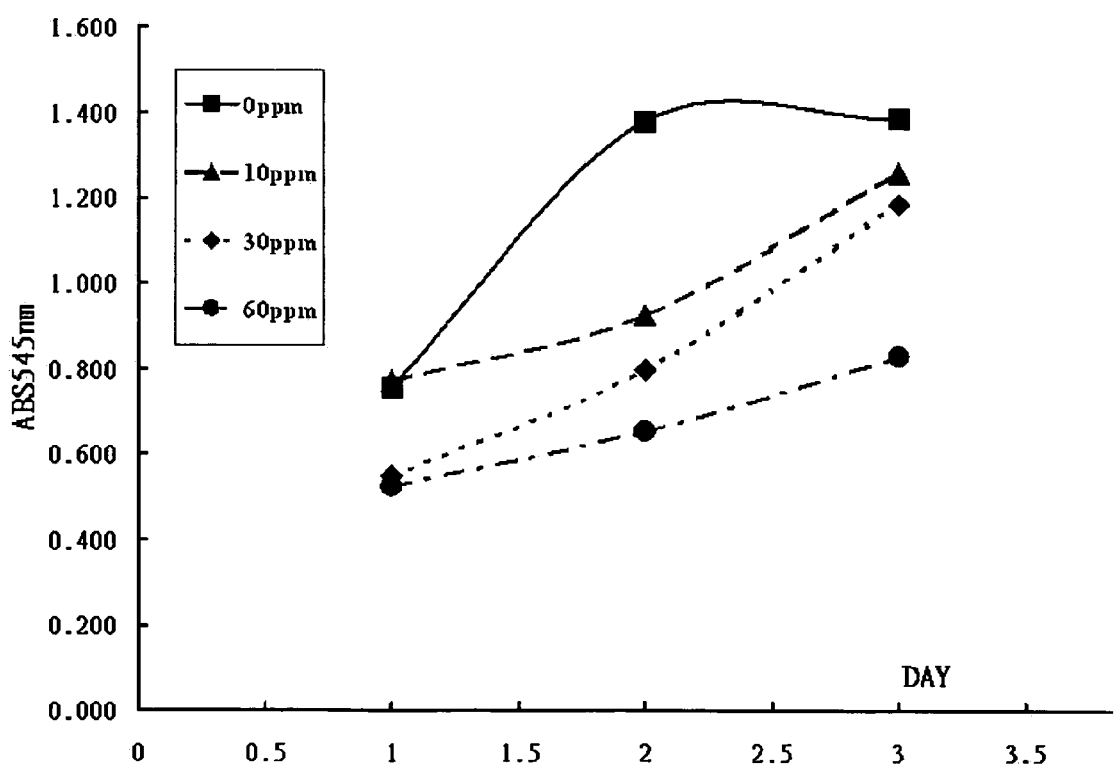
Figure 6-e (upper) and Figure 6-f (down)

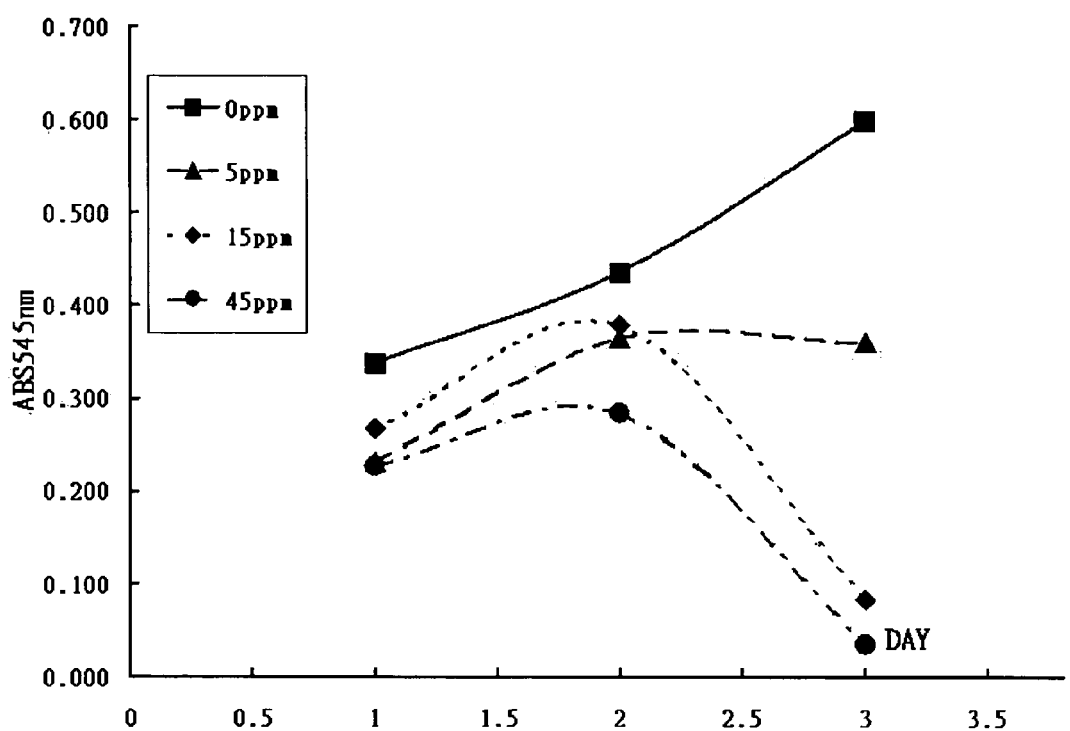
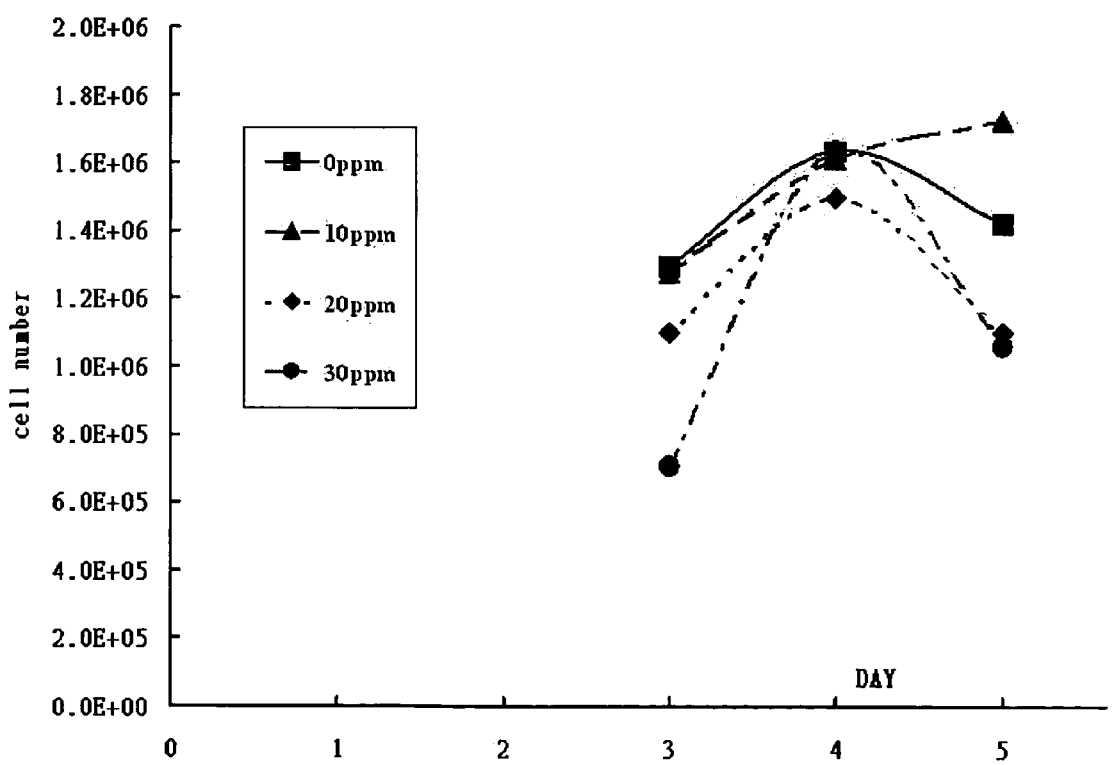
Figure 7-a (upper) and Figure 7-b (down)

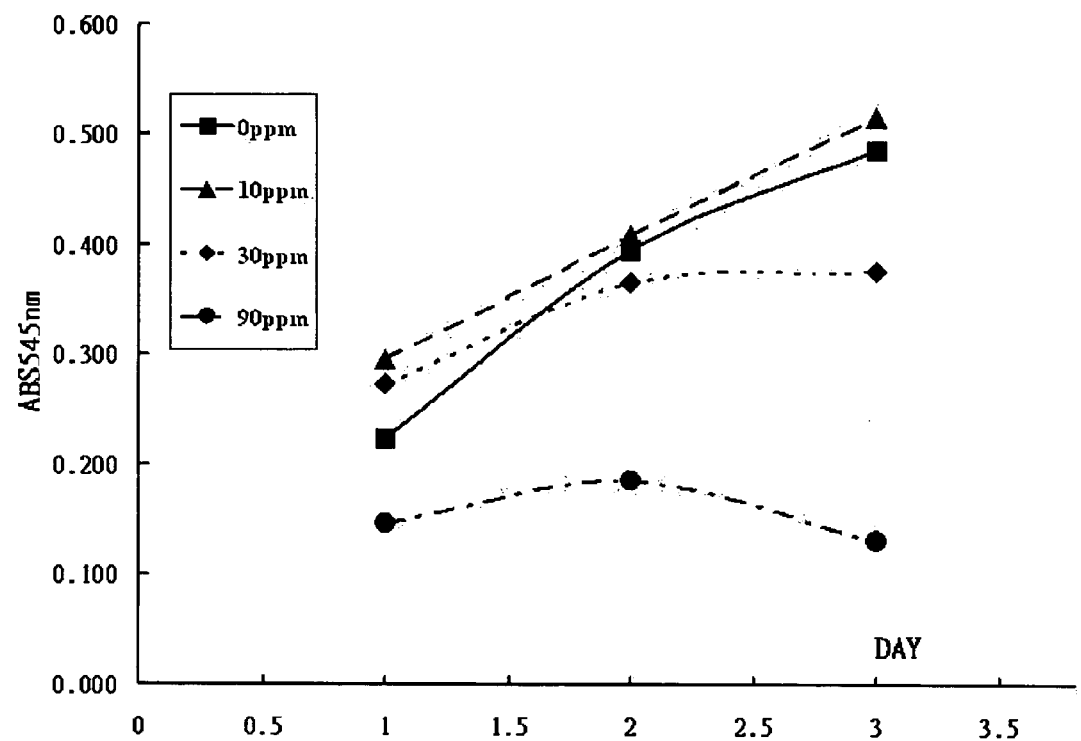
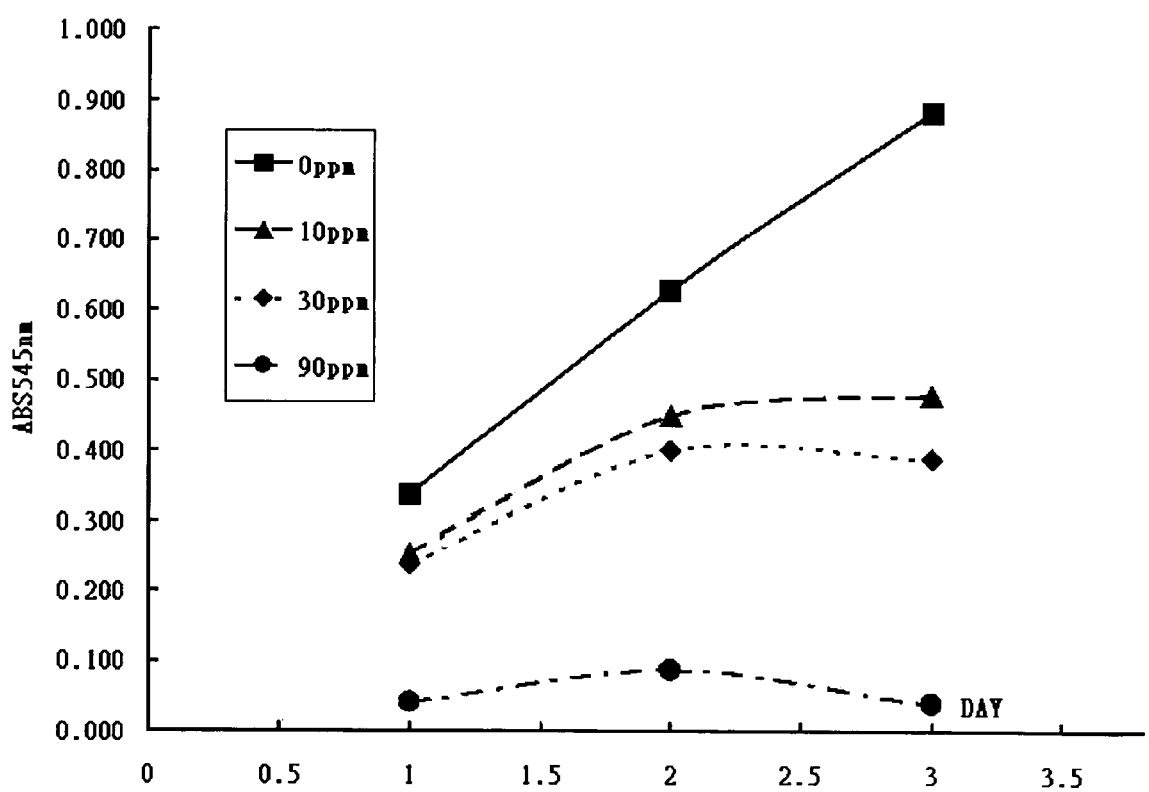
Figure7-c (upper) and Figure7-d (down)

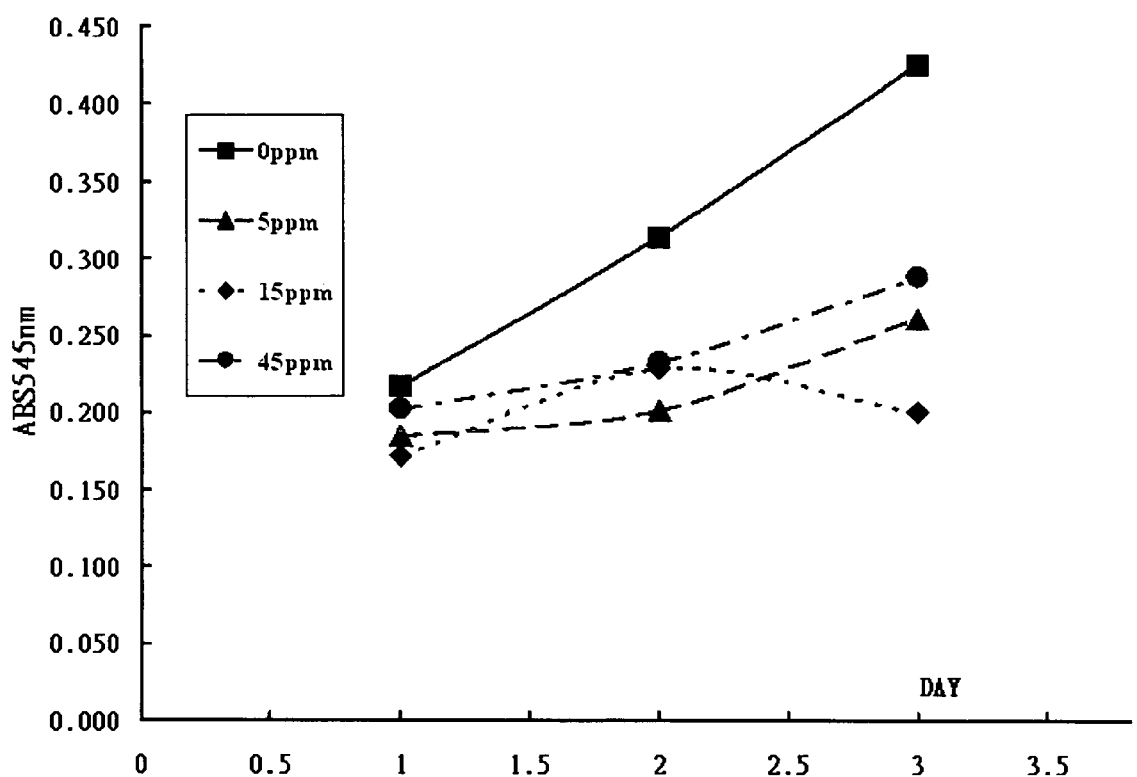
Figure 7-e

COMPOUNDS FROM *ANTRODIA CAMPHORATA* HAVING ANTI-INFLAMMATORY AND ANTI-TUMOR ACTIVITY

FIELD OF THE INVENTION

The present invention relates to novel mixture and compounds from mycelium of *Antrodia Camphorata* and the use thereof. The present invention relates to the composition or mycelium comprising the compounds of the invention.

BACKGROUND OF THE INVENTION

The fruiting body of *Antrodia camphorata* (Polyporaceae, Aphyllophorales) is well known in Taiwan as a traditional Chinese medicine. It grows only on the inner heartwood wall of the endemic evergreen *Cinnamomun kanehirai* (Hay) (Lauraceae) in Taiwan. It is rare and has not been cultivated. The fruiting bodies have been used for treating of food and drug intoxication, diarrhea, abdominal pain, hypertension, itchy skin, and liver cancer. Very few biological activity studies have been reported hitherto.

*Antrodia camphorata* also known as "niu-chang-chih" or "niu-chang-ku" in Taiwan, was recently reported as a new fungus species characterized by the cylindrical shape of its basidiospores appearing in fruiting bodies, weakly amyloid skeletal hyphae, bitter taste and light cinnamon resupinate to pileate basidiocarps, as well as chlamydospores and anthroconidia in pure culture. The growth of this new fungus species is extremely slow and restricted to an endemic tree species, *Cinnamomum kanehirai* Hay (Lauraceae), as the only host. The detailed characterization and taxonomic position of *Antrodia camphorata* were described in Wu, S.-H., et al., *Antrodia cinnamomea* ("niu-chang-chih"), New combination of a medicinal fungus in Taiwan, Bot. Bull. Acad. Sin. 38: 273–275 (1997).

In Taiwanese folk medicine, the fruiting bodies of *Antrodia camphorata* are believed to have certain medical effects. According to the traditional way, the fruiting bodies are ground into dry powder or stewed with other herbal drugs for oral uptake to treat conditions caused by poisoning, diarrhea, abdominal pain, hypertension, skin itches and liver cancer. However, few pharmacological or clinical study in these aspects has appeared in literature to date. Because of the stringent host specificity and rarity in nature, as well as the failure of artificial cultivation, "niu-chang-chih" is very expensive in Taiwan. In recent years, the fruiting bodies of this fungus with high quality have been sold at an extremely high price of around U.S.$ 15,000 per kg.

SUMMARY OF THE INVENTION

Accordingly, an object of the present invention is to provide novel mixture from mycelium of *Antrodia Camphorata*.

Another object of the present invention is to provide novel compounds from mycelium of *Antrodia Camphorata*.

Further object of the present invention is to provide novel composition comprising the compounds of the invention.

Further object of the present invention is to provide novel mycelium of *Antrodia Camphorata* comprising the compounds of the invention.

BRIEF DESCRIPTION OF THE DRAWINGS

FIG. 4(*a*)-(*d*) shows test results of compound 3 of the invention.
FIG. 5(*a*)-(*c*) shows test results of ACM, (*Antrodia camphorata* mycelia powder) $H_2O$ Extract.
FIG. 6(*a*)-(*f*) shows test results of ACM EtOH (ethyl alcohol) Extract.
FIG. 7(*a*)-(*e*) shows test results of compound 1 of the invention.

DETAILED DESCRIPTION OF THE INVENTION

Figure 1:
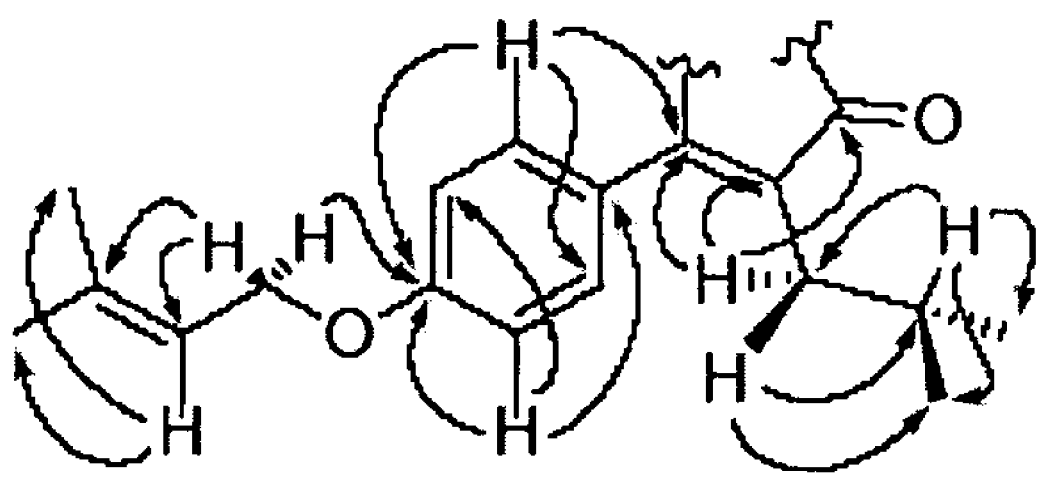
FIG. 1 shows HMBC correlations of compound 2.
Figure 2:
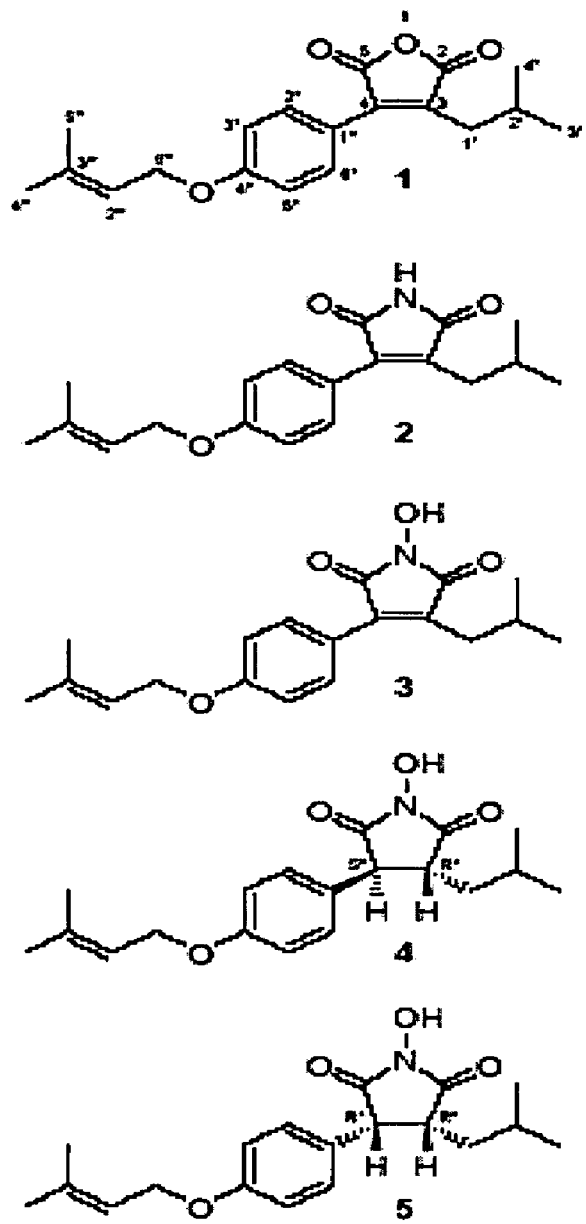
FIG. 2 shows the compounds of the invention.
Figure 3:
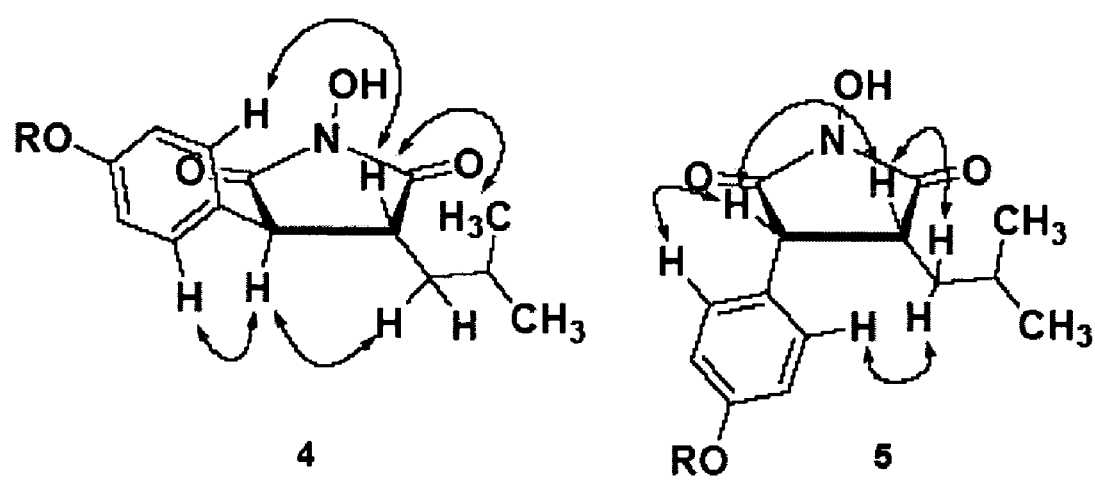
FIG. 3 shows NOE (nuclear Overhauser effect) correlations of compounds 4 and 5 of the invention.

The present invention provides a compound having the formula

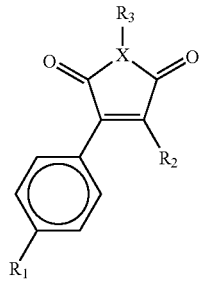

wherein
X is N or O;
$R_1$ is $C_{1-10}$ alkyloxy, $C_{2-10}$ alkenyloxy, or $C_{2-10}$ alkynyloxy;
$R_2$ is H, $C_{1-10}$ alkyl, $C_{2-10}$ alkenyl or $C_{2-10}$ alkynyl; and
$R_3$ is absent, H or hydroxy;
provided that if X is O, $R_3$ is absent.

In the compound of the invention, the preferred $R_1$ is $C_{2-6}$ alkenyloxy, or $C_{2-6}$ alkynyloxy; the more preferred $R_1$ is $C_{2-6}$ alkenyloxy substituted with $C_{1-6}$ alkyl and the most preferred $R_1$ is butenyloxy substituted with methyl. In the compound of the invention, the preferred $R_2$ is $C_{1-6}$ alkyl, the most preferred $R_2$ is isobutyl.

Accordingly, the preferred compound of the invention is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

The further preferred compound of the invention is 3-isobutyl-4-[4-(3-methyl-2-butenyloxy)phenyl]-1H-pyrrol-2,5-dione or 3-isobutyl-4-[4-(3-methyl-2-butenyloxy)phenyl]-1H-pyrrol-1-ol-2,5-dione. The further preferred compound of the invention is 3-isobutyl-4-[4-(3-methyl-2-butenyloxy)phenyl]-1H-pyrrol-1-ol-2,5-dione.

The present invention also provides a mixture from mycelium of *Antrodia Camphorata*, which comprises the compound of the invention. The mixture of the invention is prepared from water or organic solvent extract of mycelium of *Antrodia Camphorata*. The organic solvent includes but is not limited to alcohol (such as $CH_3OH$, $C_2H_5OH$, $C_3H_7OH$), ester (such as acetyl acetate), alkane (such as hexane) and halogenated alkane (such as $CH_3Cl$, $C_2H_2Cl_2$). The preferred organic solvent is ethanol or alcoholic solvent without causing any side effect of human. The mixture of the invention can decrease systolic blood pressure or increase high density lipoprotein. In addition, the same mixture has central cholinergic agonism, hepatoprotection, anti-inflammation or anti-tumor activity. Especially, the mixture of the invention can inhibit tumor from the cells or tissues selected from the group consisting of liver, intestine, bone, blood, lymph and breast. The subject accepting the mixture of the invention includes but is not limited to human, mammal, mouse, rat, horse, pig, chicken, duck, dog and cat.

The present invention also provides a composition, which comprises the compound of the invention. The composition of the invention can decrease systolic blood pressure or increase high density lipoprotein. In addition, the composition of the invention has central cholinergic agonism, hepatoprotection, anti-inflammation or anti-tumor activity. Especially, the composition of the invention can inhibit tumor from the cells or tissues selected from the group consisting of liver, intestine, bone, blood, lymph and breast. The subject accepting the composition of the invention includes but is not limited to human, mammal, mouse, rat, horse, pig, chicken, duck, dog and cat.

The present invention also provides novel mycelium of *Antrodia* comprising the compounds of the invention. The preferred mycelium has at least 1% of the weight of raw mycelium being the total weight of the compounds 1–5 of the invention. The most preferred mycelium has at least 3% of the weight of raw mycelium being the total weight of the compounds 1–5 of the invention. The mycelium of *Antrodia Camphorata* is previously prepared according to submerged liquid fermentation such as T. L. M. Stamford et al., Food Science "Protein enrichment of cashew wastes for animal feeds" from http://www.unu.edu/unupress/food/8F101e/8F101E0b.htm.

EXAMPLES

The examples below are non-limiting and are merely representative of various aspects and features of the present invention.

General Experimental Procedures.

Melting points were measured on a Yanagimoto micro hot-stage melting point apparatus and uncorrected. Optical rotations were measured with a Jasco DIP-360 automatic polarimeter. UV spectra were measured with a Shimadzu UV-2200 recording spectrophotometer. IR spectra were measured with a Jasco FT/IR-230 infrared spectrometer. $^1H$- and $^{13}C$-NMR spectrum were measured with a Varian Unity Plus 500 spectrometer. EIMS and HR-EIMS were measured with a Jeol JMS-AX 505 HAD mass spectrometer at an ionization voltage of 70 eV. Column chromatography was carried out on silica gel BW-820 MH (normal phase) and Chromatorex-ODS DM1020T (reversed phase) (Fuji Silysia).

Extraction and Isolation

*Antrodia camphorata* mycelia powder (ACM) (60 g), from Simpson Biotech Co. Ltd., Taiwan, October 2001, were three times extracted with $CHCl_3$ for 3 h under reflux. The $CHCl_3$ extract (5.3 g) was chromatographed on silica gel eluted with n-hexane-acetone (19:1–14:6), and $CHCl_3$-MeOH (1:1) to give nine fractions (Fr. 1–9). Fraction 2 was chromatographed on silica gel to give compound 1 (8.7 mg). Fraction 4 was chromatographed on normal and reversed phase silica gel to give compound 2 (13.6 mg). Fraction 5 was chromatographed on silica gel eluted with n-hexane-acetone (8:2) to give ergosterol peroxide (35.8 mg). Fraction 6 gave compound 3 (14.6 mg) by combination of normal and reversed phase silica gel column chromatography. Fraction 7 yielded a mixture of compounds 4 and 5 (4:1) by column chromatography. The mixture of compounds 4 and 5 were subsequently separated by preparative HPLC [column: Tosoh TSK-gel ODS-80T$_M$ (21.5×300 mm), mobile phase: $CH_3OH$—$H_2O$ containing 0.1% TFA (70:30)].

3-Isobutyl-4-[4-(3-methyl-2-butenyloxy)phenyl]furan-2,5-dione (compound 1):

yellow oil; UV (MeOH) $\lambda_{max}$ (log ε) 227 (4.1), 258 (3.9), 275 (3.8), 355 (3.4) nm; IR ($CHCl_3$) $\nu_{max}$ 1763 cm$^{-1}$; $^1H$-NMR Table 1; $^{13}C$-NMR Table 2; EIMS m/z 314 [M]$^+$ (100), 246 (100), 131 (100); HR-EIMS m/z 314.1523 (Calcd for $C_{19}H_{22}O_4$, 314.1518).

3-Isobutyl-4-[4-(3-methyl-2-butenyloxy)phenyl]-1H-pyrrole-2,5-dione (2):

yellow needles (n-hexane-AcOEt); mp 110–111° C.; UV (MeOH) $\lambda_{max}$ (log ε) 230 (4.3), 272 (3.5), 355 (3.7) nm; IR ($CHCl_3$) $\nu_{max}$ 1724 cm$^{-1}$; $^1H$-NMR Table 1; $^{13}C$-NMR Table 2; EIMS m/z 313 [M]$^+$ (8), 245 (100), 203 (77), 131 (28); HR-EIMS m/z 313.1681 (Calcd for $C_{19}H_{23}NO_3$, 313.1678).

X-ray Crystallography of Compound 2:

Yellow needles were obtained by crystallization from n-hexane-AcOEt and selected for data collection. Crystal data: $C_{19}H_{23}NO_3$; $M_r$=313.40; dimensions 0.15×0.02×0.02 mm; triclinic, space group P1 (#2), a=6.3505(5) Å, b=12.205(1) Å, c=12.560(2) Å, α=64.623(7)°, β=75.358(4)°, γ=84.681(5)°, V=850.9(2) Å$^3$, Z=2, $D_{calc}$=1.223 g/cm$^3$, μ(MoKα)=0.82 cm$^{-1}$, $F_{000}$=336.00. Measurement was made on a Rigaku RAXIS-RAPID Imaging Plate diffractometer with graphite monochromated Mo-Kα (λ=0.71069 Å) radiation at 93 K. Of the 8950 reflections which were collected, 4745 were unique ($R_{int}$=0.108); equivalent reflections were merged. The crystal structure was solved by direct methods (SHELXS86) and refined by full-matrix least-squares. The non-hydrogen atoms were refined anisotropically. Hydrogen atoms were included but not refined. The final indices were R=0.074, $R_w$=0.099, with GOF (Guest Observer Facility)=1.06. The maximum and minimum peaks on the final difference Fourier map corresponded to 0.83 and −0.89 e$^-$/Å$^3$, respectively.

3-Isobutyl-4-[4-(3-methyl-2-butenyloxy)phenyl]-1H-pyrrol-1-ol-2,5-dione (Compound 3): yellow oil; UV (MeOH) $\lambda_{max}$ (log ε): 232.5 (4.3), 296 (3.7), 374 (3.7) nm; IR ($CHCl_3$) $\nu_{max}$ 1717 cm$^{-1}$; $^1H$-NMR Table 1; $^{13}C$-NMR Table 2; EIMS m/z 329 [M]$^+$ (12), 261 (100), 131 (50); HR-EIMS m/z: 329.1637 (Calcd for $C_{19}H_{23}NO_4$, 329.1627).

3R*,4S*-1-Hydroxy-3-isobutyl-4-[4-(3-methyl-2-butenyloxy)phenyl]pyrrolidine-2,5-dione (4): colorless oil; $[α]_D^{23}$+2.5° (c 0.2, MeOH); UV (MeOH) $\lambda_{max}$ (log ε): 225 (4.3), 275 (3.3), 283 (3.2) nm; IR ($CHCl_3$) $\nu_{max}$ 1715 cm$^{-1}$; $^1H$-NMR Table 1; $^{13}C$-NMR Table 2; EIMS m/z 331 [M]+ (2), 263 (67), 207 (66), 191 (30), 179 (40), 133 (64), 69 (100); HR-EIMS m/z 331.1747 (Calcd for $C_{19}H_{25}NO_4$, 331.1783).

3R*,4R*-1-Hydroxy-3-isobutyl-4-[4-(3-methyl-2-butenyloxy)phenyl]pyrrolidine-2,5-dione (5): colorless oil; $[α]_D^{23}$+3.0° (c 0.2, MeOH); UV (MeOH) $\lambda_{max}$ (log ε): 227 (4.3), 275 (3.4), 283 (3.3) nm; IR ($CHCl_3$) $\nu_{max}$ 1715 cm$^{-1}$; $^1H$-NMR Table 1; $^{13}C$-NMR Table 2; EIMS m/z 331 [M]$^+$ (1), 263 (45), 207 (50), 191 (75), 179 (30), 133 (100), 69 (92); HR-EIMS m/z 331.1766 (Calcd for $C_{19}H_{25}NO_4$, 331.1783).

Ergosterol peroxide: colorless needles (n-hexane-acetone); mp 165–169° C. (lit[2] mp 171–174° C.).

Cytotoxic Assays. The in vitro LLC tumor cell assay was carried out by sulforhodamin B (SRB) method. The 50% growth inhibition ($ED_{50}$) was calculated by Probit method.

Results and Discussion

The $CHCl_3$ extract of the mycelium of *Antrodia Camphorata* was repeatedly hromatographed on normal and reversed phase silica gel to afford five new maleic and succinic acid derivatives (compounds 1–5) together with ergosterol peroxide.

Table 1 absorption at 1724 $cm^{-1}$. The $^{13}$C-NMR spectrum showed signals of four methyl carbons, two methylene carbons, and one methine carbon in the aliphatic region, as well as one benzene ring, one olefinic group and two carbonyl carbons. The $^1$H-NMR spectrum showed the presence of an isobutyl moiety at δ 0 0.90, 2.06, and 2.51, a 3-methyl-2-butenyloxy moiety at δ 1.76, 1.81, 4.56, and 5.50, and a para-substituted benzene moiety at δ 6.95 and 7.50, which was further supported by $^1$H—$^1$H COSY (cooler synchrotron) and HMQC (heteronuclear multiple quantum coherence) experiments. Long range correlations were observed by HMBC as shown in FIG. 1. On the basis of the molecular formula and

TABLE 1

$^1$H-NMR Spectral Data of Compounds 1–5 (δ ppm, J=Hz) (500 MHz, $CDCl_3$)

| H | 1 | 2 | 3 | 4 | 5 |
|---|---|---|---|---|---|
| 3 | — | — | — | 2.87(1H, m) | 3.08(1H, m) |
| 4 | — | — | — | 3.52(1H, d, J=4.0) | 4.07(1H, d, J=8.0) |
| 1' | 2.59(2H, d, J=7.0) | 2.51(2H, d, J=7.0) | 2.50(2H, d, J=7.0) | 1.51(1H, m) 1.72~1,84(1H) | 1.02(1H, m) 1.42~1.48(1H) |
| 2' | 2.12(1H, sep, J=7.0) | 2.06(1H, sep, J=7.0) | 2.05(1H, sep, J=7.0) | 1.72~1.84 (1H) | 1.42~1.48 (1H) |
| 3' | 0.94(6H, d, J=7.0) | 0.90(6H, d, J=7.0) | 0.88(6H, d, J=7.0) | 0.70(3H, d, J=6.5) | 0.66(3H, d, J=6.5) |
| 4' | | | | 0.89(3H, d, J=6.5) | 0.80(3H, d, J=6.5) |
| 2", 6" | 7.50(2H, d, J=9.0) | 7.50(2H, d, J=9.0) | 7.50(2H, d, J=9.0) | 7.07(2H, d, J=8.5) | 6.96(2H, d, J=9.0) |
| 3", 5" | 7.02(2H, d, J=9.0) | 6.95(2H, d, J=9.0) | 6.98(2H, d, J=9.0) | 6.87(2H, d, J=8.5) | 6.84(2H, d, J=9.0) |
| 1''' | 4.57(2H, d, J=6.6) | 4.56(2H, d, J=6.5) | 4.55(2H, d, J=6.9) | 4.47(2H, d, J=6.5) | 4.47(2H, d, J=6.5) |
| 2''' | 5.50(1H, brt, J=6.6) | 5.50(1H, brt, J=6.5) | 5.49(1H, brt, J=6.9) | 5.47(1H, brt, J=6.5) | 5.47(1H, brt, J=6.5) |
| 4''' | 1.81(3H, s) | 1.81(3H, s) | 1.81(3H, s) | 1.79(3H, s) | 1.79(3H, s) |
| 5''' | 1.76(3H, s) | 1.76(3H, s) | 1.76(3H, s) | 1.73(3H, s) | 1.73(3H, s) |

TABLE 2

$^{13}$C-NMR Spectral Data for Compound 1–5 (δ ppm) (125 MHz, $CDCl_3$)

| C | 1 | 2 | 3 | 4 | 5 |
|---|---|---|---|---|---|
| 2 | 166.4 (s) | 171.7 (s) | 168.8 (s) | 174.8 (s) | 175.1 (s) |
| 3 | 139.8 (s) | 138.8 (s)[a] | 135.9 (s)[a] | 44.6 (d) | 40.3 (d) |
| 4 | 140.2 (s) | 139.2 (s)[a] | 136.0 (s)[a] | 49.8 (d) | 47.5 (d) |
| 5 | 165.4 (s) | 171.1 (s) | 168.1 (s) | 173.2 (s) | 173.6 (s) |
| 1' | 33.6 (t) | 32.8 (t) | 33.2 (t) | 40.4 (t) | 35.3 (t) |
| 2' | 27.9 (d) | 28.1 (d) | 28.4 (d) | 25.3 (d) | 25.2 (d) |
| 3' | | | | 21.3 (q) | 21.8 (q) |
| 4' | 22.7 (q) | 22.7 (q) | 23.0 (q) | 23.0 (q) | 22.4 (q) |
| 1" | 119.9 (s) | 121.2 (s) | 120.8 (s) | 127.9 (s) | 125.1 (s) |
| 2", 6" | 131.1 (d) | 130.9 (d) | 131.0 (d) | 128.8 (d) | 130.2 (d) |
| 3", 5" | 115.1 (d) | 114.9 (d) | 115.0 (d) | 115.4 (d) | 115.0 (d) |
| 4" | 160.9 (s) | 160.1 (s) | 160.2 (s) | 158.7 (s) | 158.7 (s) |
| 1''' | 65.0 (t) | 64.9 (t) | 65.1 (t) | 64.1 (t) | 64.8 (t) |
| 2''' | 118.7 (d) | 119.3 (d) | 119.2 (d) | 119.4 (d) | 119.3 (d) |
| 3''' | 139.1 (s) | 138.6 (s)[a] | 138.9 (s) | 138.3 (s) | 138.4 (s) |
| 4''' | 25.2 (q) | 25.8 (q) | 26.1 (q) | 25.8 (q) | 25.8 (q) |
| 5''' | 18.2 (q) | 18.2 (q) | 18.5 (q) | 18.1 (q) | 18.2 (q) |

[a] Assignments may be interchangeable.

The structures of the new compounds were determined as follow: Compound 2 gave yellow needles, mp 110–111° C., and the molecular formula $C_{19}H_{23}NO_3$ was assigned by HR-EIMS. The IR spectrum showed an imide carbonyl the $^{13}$C-NMR spectrum, this compound was deduced to contain further CHNO atoms, including one more carbonyl carbon. Thus, this ambiguous part was speculated to be a maleimide group. This structure was then established to be 3-isobutyl-4-[4-(3-methyl-2-butenyloxy)phenyl]-1H-pyrrole-2,5-dione by X-ray analysis.

The molecular formula of compound 1 was assigned as $C_{19}H_{22}O_4$ by HR-EIMS. The IR spectrum revealed a carbonyl absorption of acid anhydride at 1763 $cm^{-1}$. The $^1$H-NMR spectrum of compound 1 was similar to that of compound 2, and showed the presence of an isobutyl moiety, a 3-methyl-2-butenyloxy moiety, and a para-substituted benzene ring. From the HMBC spectrum, compound 1 was demonstrated to have the same partial structure to compound 2 (FIG. 1), in which the presence of a maleic anhydride group was deduced on the basis of the molecular formula compound 1 was consequently determined as 3-isobutyl-4-[4-(3-methyl-2-butenyloxy)phenyl]furan-2,5-dione.

The molecular formula of compound 3 was assigned as $C_{19}H_{23}NO_4$ by HR-EIMS. The IR spectrum showed a carbonyl absorption at 1717 $cm^{-1}$, assignable to a hydroxy imide. The $^1$H- and $^{13}$C-NMR spectra were also similar to those of compounds 1 and 2, and showed the presence of an isobutyl moiety, a 3-methyl-2-butenyloxy moiety, and a para-substituted benzene ring. In the HMBC experiment, compound 3 was shown to have the same partial structure as compound 2 (FIG. 1). Compound 3 contains one more oxygen atom than compound 2, therefore, this compound was determined to be (3-isobutyl-4-[4-(3-methyl-2-butenyloxy)phenyl-1H-pyrrol-1-ol-2,5-dione.

Compounds 4 and 5 had the same $R_f$ values and the same molecular formula by HR-EIMS ($C_{19}H_{25}NO_4$, found 331.1747 and 331.1766, respectively), however, they could be separated by preparative HPLC. The IR spectrum of both compounds showed a hydroxy imide carbonyl absorption at 1715 cm$^{-1}$. In the 1H- and $^{13}$C-NMR spectra, both compounds showed the presence of an isobutyl moiety, a 3-metyl-2-butenyloxy moiety, and a para-substituted benzene ring, but the isobutyl methylene protons displayed a multiplet and not a doublet as for compounds 1–3. The $^1$H-$^1$H COSY spectrum indicated that this methylene group is attached to a —CH—CH— unit. The $^{13}$C-NMR spectra of compounds 4 and 5 exhibited two additional sp$^3$ carbon signals, replacing two sp$^2$ carbon signals observed for compounds 1–3. Therefore, compounds 4 and 5 were not N-hydroxy maleimides, but rather N-hydroxy succinimides, with stereocenters at positions C-3 and C-4 in the succinimide ring. Compounds 4 and 5 were determined to be trans and cis isomers, respectively, from the coupling constant between H-3 and H-4 (4.0 and 8.0 Hz for compounds 4 and 5, respectively). No NOE was observed between H-3 and H-4 in the NOESY (Nuclear Overhauser Effect Spectroscopy) spectrum of compound 4, while appreciable NOE was observed in that of compound 5. The optical rotations of compounds 4 and 5 showed +2.5° and +3.0°, respectively, while their CD spectra showed no Cotton effects at any wave length, suggesting that both compounds 4 and 5 are racemic mixtures. Resolution of these racemic mixtures by HPLC using a chiral column with several solvent systems was unsuccessful. At present, we cannot definitely conclude whether these compounds are optically active compounds or racemic mixtures. Thus, their relative structures were determined as 3R*,4S*- and 3R*,4R*-1-hydroxy-3-isobutyl-4-[4-(3-methyl-2-butenyloxy)phenyl]pyrrolidine-2,5-dione, respectively.

Isolation of these type of maleic and succinic acid derivatives from nature were second time followed by the report of Aquveque et al.

The cytotoxic activity of the chloroform extract and isolated compounds were investigated using LLC (Lewis lung carcinoma) cell line (Table 3). The chloroform extract showed moderate cytotoxic effects with an ED$_{50}$ value of 26.7 μg/ml. Maleic compounds 1 and 4 had no cytotoxic activity, whereas compounds 2 and 3 were found to be cytotoxic to the LLC cell line with ED$_{50}$ values lower than that of the chloroform extract.

TABLE 3

50% Growth Inhibition (ED$_{50}$) Values of the CHCl$_3$ Extract and Compounds 1–4 from the mycelia of *Antrodia Camphorata* against LLC Cell Line

| | ED$_{50}$ (μg/ml) |
|---|---|
| CHCl$_3$ extract | 26.7 |
| 1 | >20 |
| 2 | 3.6 |
| 3 | 7.5 |
| 4 | >10 |
| Adriamycin[a] | 0.14 |

[a]Positive control.

Tumor Assay of ACM (*Antrodia camphorata* Mycelia Powder)

A. Cell line
　Adherent cell
　MCF-7 human breast carcinoma
　HT-29: human colon adenocarcinoma
　KATO III: human stomach carcinoma
　SW480: human colon adenocarcinoma
　SW620: human colon adenocarcinoma
　HepG2: human liver carcinoma
　Suspension cell:
　EL4: mice lymphoma B. Samples
　Compound 1, Compound 3, ACM EtOH Extract, ACM H$_2$O Extract C. Assay method
　Calculate ED$_{50}$ (50% inhibition of effective dose
　Adherent cell: MTT (methyl thiazolyl tetrazolium) method; for MCF-7, HT-29, KATO II1, SW480, HepG2, cells are determined at 3 days. SW620 at 4 days
　Suspension cell: Cell count method; EL4 cells count at 5 days D. Result
　Calculation:

$y = m\, Ln(x) + b$

EXAMPLE

| X | Y |
|---|---|
| 0 | 0.97 |
| 10 ppm | 0.941 |
| 30 ppm | 0.6 |
| 100 ppm | 0.331 |

Use value of X (10, 30, 50 ppm) and Y to get correlation curve $y = -0.2643 Ln(x) + 1.5321$ $ED_{50} = \exp[(0.97/2 - 1.5321)/(-0.2643)]$ Sample Preparation and Sample Description A. ACM (*Antrodia Camphorata* Mycelia Powder) H$_2$O Extract
　1. Add 1 g of ACM into 40 ml of RO H$_2$O in a 250 ml beaker, put the beaker in ultrasonic water bath for 20 min at room temperature
　2. Stir at 45° C. water bath for 45 min
　3. Place the beaker in ultrasonic water bath for another 20 min
　4. Centrifuge the sample at 3000 rpm for 15 min
　5. Collect supernatant and perform serial dilutions with media.

B. Determination of Sample Concentration
　1. Weigh an evaporating dish (W1)
　2. Add 10 ml of H$_2$O extract sample in the evaporating dish
　3. Place the evaporating dish in the oven to remove water W2)

Sample weight/ml = (W2 − W1)/10

C. ACM (*Antrodia Camphorata* Mycelia Powder) EtOH Extract
  1. Add 100 ml of 95% alcohol to 20 g ACM in a 500 ml beaker and stir for 10 min at room temperature
  2. Filter the suspension through Advantec # 1 filter paper, and collect the filtrate
  3. Concentrate the filtrate by rotary vacuum evaporator to remove alcohol.
D. Compound 1 Pure compound from ACM
E. Compound 3 Pure compound from ACM MTT Assay Method
  1. Discard old media after cell proliferation, then wash cells once with phosphate-buffered saline (PBS) once
  2. Wash down the cells with trypsin-EDTA
  3. Centrifuge at 1200 rpm for 5 min, then discard supernatant
  4. Suspend the pellet with 10 ml medium
  5. Mix 100 µl cell suspension with 100 µl trypan blue to calculate viable cells
  6. Add $1*10^4$ cells/100 µl medium in each well of the 96 well plate, incubate the plate$CO_2$ incubater at 37° C. for 24 hrs
  7. Discard old medium, wash cells once with PBS
  8. Add 100 µl sample in each well, incubate the plate in $CO_2$ incubater at 37° C.
  9. Wash cells once with PBS at 3rd, 4th and 5th days,
  10. Add 57 µl MTT (0.88 mg/ml) in each well
  11. After 4 hrs discard MTT and wash cells with PBS once
  12. Add 50 µl DMSO/Well
  13. Read at OD545 on Elisa reader Cell Count Method (EL4 Cell Line)
  1. Discard old media after cell proliferation by centrifugation
  2. Resuspend the pellet with fresh medium
  3. Mix 100 µl cell suspension with 100 µl trypan blue to calculate viable cells
  4. Prepare different concentration of samples that contain $1*10^5$ cell/ml sample
  5. Load 100 µl sample in each well of the 96 well plate, incubate the plate at 37° C. $CO_2$ incubater
  6. Calculate viable cells at 3rd, 4th and 5th days

| PBS | |
|---|---|
| NaCl | 8 g |
| KCl | 0.2 g |
| $Na_2HPO_4$ | 1.4 g |
| $KH_2PO_4$ | 0.2 g |
| Make volume to 1 L | PH 7.4 |

Result and Discussion

Deatiled test results as follows:

Compound 3 of the invention: HepG2 (FIG. 4a), EL4 (FIG. 4b), HT-29 (FIG. 4c) and Kato III (FIG. 4d).

ACM $H_2O$ Extract: HepG2 (FIG. 5a), SW620 (FIG. 5b) and EL4 (FIG. 5c).

ACM EtOH Extract: HT-29 (FIG. 6a), SW480 (FIG. 6b), SW620 (FIG. 6c), EL4 (FIG. 6d), HepG2 (FIG. 6e) and Kato III (FIG. 6f).

Compound 1 of the invention: MCF-7 (FIG. 7a), EL4 (FIG. 7b), HT-29 (FIG. 7c), SW620 (FIG. 7d) and HepG2 (FIG. 7e).

Given the above, it demonstrates that the compounds and ACM Extract of the invention have inhibition effect on various types of tumor cells.

Analysis of All New Compounds (1, 2 and 3) from ACM EtOH Extract by High Performance of Liquid Chromatography Method Purpose: In order to measure the amount of all new compounds (1, 2 and 3) from ACM EtOH Extract, High Performance of Liquid Chromatography was employed as our routine quality control procedures.

Preparation for ACM EtOH Extract Sample
  1), By using digital balance precisely weight 20.000(g) of sample powders in a graduated media lab bottle with 100 mL of 95% alcohol, and do not screw the lid tightly on.
  2), Place above step of the sample bottle in ultrasonic water bath 10 minutes.
  3), Pour liquid samples to centrifuge tubes, and then place those samples in a centrifuge remove crude particle, under condition of 6500 rpm/5 minutes.
  4), Filter liquid layer with filter paper, advantec No. 1.
  5), Concentrate filtering solution by rotary vacuum evapotator until appear a thick, yellowish liquid, alcohol free.
  6), Repeat three times of step 1 to 5, and then collect all extract product (total ACM EtOH Extract=4.60 g). Calculate yield.

Application By Water HPLC, Model 2690:
  1), Column: Reverse Phase C18
  2), Mobile Phase MeOH, $H_2O$, acetonitrile
  3), Injection vol 20 µL
  4), Detection: Photodiode Array Detector 996 on wavelength 254 nm
  5), Preparation 1.000 (g) ACM EtOH Extract sample in 10 mL of alcohol for HPLC analysis*:

Results: according to HPLC analysis, the extract product contains pure compound 1, 2, and 3 was showed in following Table 4

| $ED_{50}$ of ACM on Cell Lines | | | | | | | |
|---|---|---|---|---|---|---|---|
| Cell line | HepG2 | HT-29 | KATO III | EL4 | SW480 | SW620 | MCF-7 |
| Compound 1 | 21 ppm | 52 ppm | 38 ppm | 3.5 ppm | | 15 ppm | 6 ppm |
| Compound 3 | 35 ppm | 42 ppm | 69 ppm | 2.6 ppm | 20 ppm | 27 ppm | 0.02 ppm |
| ACM EtOH Extract | 32 ppm | 52 ppm | 156 ppm | 2.6 ppm | 71 ppm | 4 ppm | |
| ACM $H_2O$ Extract | 295 ppm | 707 ppm | | 20 ppm | 207 ppm | 132 ppm | 318 ppm |

TABLE 4

| Standard Name | Compound 1 | Compound 2 | Compound 3 |
|---|---|---|---|
| For ingredients of three standard compounds: weight 0.0100 (g) in 1 mL of alcohol | | | |
| Concentration (g/mL) | 0.01 | 0.01 | 0.01 |
| Peak Area | 49,315,783 | 129,327,136 | 136,255,406 |
| Retention time (min) | 134.8 | 124.3 | 119.8 |
| *For ACM EtOH Extract sample: weight 1,000 (g) in 10 mL of alcohol | | | |
| Concentration (g/mL) | $8.59 \times 10^{-3}$ | $5.59 \times 10^{-4}$ | $1.659 \times 10^{-2}$ |
| Peak Area | 42,374,766 | 7,226,937 | 226,102,223 |
| Percentage yield % (w/w) | 8.59 | 0.559 | 16.59 |

Therefore, the total weight of compounds 1, 2 and 3 is 5.92% by weight in ACM sample.

Tests for ACM-EtOH Extract

Materials and Equipment

1. Test Substances and Dosing Pattern

Test substance was administered orally at an initial dose of 1000 mg/kg for all in vivo assays in a vehicle of 2% Tween 80. Time of observation for each assay was described in methods.

2. Animals

Male or female ICR mice, Wistar-Okamoto derived male spontaneously hypotensive rat (SHR), Wistar and Long Evans derived rats provided by MDS Pharma Services Taiwan Ltd. were used. Space allocation for animals was as folloes: 29×18×13 cm for 10 mice, 45×23×21 cm for 6 rats, and 45×23×21 cm for 3 guinea pigs. Mice and rats were housed in APEC$^R$ cages. The immunocompetent C57BL/6J male mice, 6–8 weeks age, weighing 21±2 gm were also used in this study and provided by National Taiwan University Animal Center. The animals were housed in Individually Ventilated Cages Racks (IVC racks, 36 Mini Isolator System). Each cage was sterilized by autoclave and contained 5 mice (in 26.7×20.7×14 cm). All animal were maintained in a controlled temperature (21°–23° C.) and humidity (60%–70%) environment with 12 hour light dark cycles for at least one week in the laboratory prior to use. Free access to standard lab chow (LabDiet Rodent Diet and Guinea Pig Diet, PMI Nutrition International, USA) and tap water was granted.

3. Cell Line and Culture Media

The murine melanoma cell line, B16-F0 (ATCC CRL-6322), was purchased from American Type Culture Collection and Dulbecco's Modified Eagle's Medium (GIBCO, USA) was used as culture medium. The tumor cells were incubated in an atmosphere containing 5% $CO_2$ at 37° C.

4. Chemicals

General:

Distilled Water (In-house), Dimethyl Sulfoxide (DMSO, Merck, Germany), Isotonic Sodium Chloride Solution (Sintong Chemical Industry Co. Ltd., R.O.C.), magnesium Sulfate ($MgSO_4.7H_2O$, Wako, Japan), Meclofenamate Sodium (Sigma, USA), Methylcellulose (Signa, USA), Sodium Hydroxide (NaOH, Wako, Japan), Phosphate Buffered Saline (Sigma, USA) and Tween 80 (Wako, Japan).

Reagents

Glicose-HA assay kit (Wako, Japan), Alanine aminotransferase (ALT) assay kit (Wako, Japan), Aspartate aminotransferase (AST) assay kit (Wako, Japan), T-Cholesterol-HA and HDL assay kit (Wako, Japan), Hemolynac 3 Hemolys (Nihon Koden, Japan), Isotonic 3 Diluent (Nihon Koden, Japan).

5. Equipment

General Use:

Animal Case (ShinTeh, R.O.C.), Beaker 250 ml and 1000 ml (Kinmax, USA), disposable syringe (1 ml, Top Corporation, Japan), Forceps stainless (klappencker, Germany), Mouse scale #Z-40 (Taconic, USA), needle for oral administration (Natsune, Japan), Needle Hypodermic 23 G×1" (Top Corporation, Japan), pH Meter (Suntex, USA), Rat scale 500 g±2 g (Chien-chun, ROC), syringe Glass 1 ml, 2 ml and 5 ml (Mitsuba, Japan), and Scissors Stainless (Klappencker, Germany).

Methods and Results:

1. Cholinergic Agonism, Central/Peripheral (Lippmann W and Pugsley T A. Arch Int Pharmacodyn. 227:324, 1977)

Test substance was administered orally to a group of 3 Wistar derived male or female rats weighing 150±20 g. During the subsequent 30–60 minute period, the number of animals exhibiting more than 10 seconds of chewing behavior (mouth and/or tongue movements) measured cumulatively and the number of animals exhibiting salivation or exhibiting salivation were noted. Positive responses observed in 2 or more ($\geq 2$) of 3 rats indicates possible central cholinergic activity and peripheral cholinergic activity.

TABLE 5

Result of Cholinergic Agonism, Central/peripheral in Rats

| Treatment | Route | Dose | | N | Central Chewing | Score | Peripheral Salivation | Score |
|---|---|---|---|---|---|---|---|---|
| Vehicle | PO | 10 | ml/kg | 1 | – | | – | |
| | | | | 2 | – | | – | |
| | | | | 3 | – | 0/3 | – | 0/3 |
| ACM-EtOH Extract | PO | 1000 | mg/kg | 1 | + | | – | |
| | | | | 2 | + | | – | |
| | | | | 3 | + | (3/3) | – | 0/3 |
| | | 300 | mg/kg | 1 | – | | – | |
| | | | | 2 | – | | – | |
| | | | | 3 | + | 1/3 | – | 0/3 |
| Arecoline-HBR | IP | 30 | mg/kg | 1 | + | | + | |
| | | | | 2 | + | | + | |
| | | | | 3 | + | (3/3) | + | (3/3) |

Vehicle and test substances were administered orally (PO) while the positive reference compound was injected intraperitoneally (IP). During the subsequent 30–60 minute period, the number of animal exhibiting more than 10 seconds of chewing behavior (mouth and/or tongue movements) measured cumulatively or exhibiting salivation were noted. Positive responses observed in 2 or more ($\geq 2$) of 3 rats indicates possible cholinergic activity or peripheral cholinergic activity.

2. Cardiovascular, Blood Pressure and Heart rate (SHR 0, 1, 2, 4 hrs) (Yen T T et al. Life Sci. 22: 359, 1978)

Groups of 3 Wistar-Okamoto derived male spontaneously hypertensive rats (SHR) weighting 250±20 g were used; the mean systolic blood pressure was 200±20 mmHg and heart rate 400±30 beats/min. Blood pressure and heart rate were recorded indirectly by tail cuff method in a temperature controlled environment (32±1° C.) before (0 time) and 1, 2 and 4 hours after oral administration of test substance or vehicle. A reduction in systolic pressure by 10 percent or more ($\geq 10\%$), or decrease in heart rate by 20 percent or more ($\geq 20\%$), at each measured time interval relative to 0 time, is considered significant.

TABLE 6

Result of Cardiovascular, Blood Pressure (SHR 0, 1, 2, 4 Hours) in Rats

| | | | | % Control (from 0 times) | | |
|---|---|---|---|---|---|---|
| Treatment | Route | Dose | N | 1 Hour | 2 Hours | 4 Hours |
| Vehicle | PO | 10 ml/kg | 1 | 100 | 96 | 90 |
| | | | 2 | 97 | 100 | 91 |
| | | | 3 | 90 | 92 | 92 |
| | | | Ave. | 96 | 96 | 91 |
| ACM-EtOH Extract | PO | 1000 mg/kg | 1 | 78 | 85 | 71 |
| | | | 2 | 86 | 89 | 80 |
| | | | 3 | 89 | 89 | 89 |
| | | | Ave. | (84) | (88) | (80) |
| Clonidine | PO | 0.1 mg/kg | 1 | 71 | 67 | 71 |
| | | | 2 | 95 | 86 | 88 |
| | | | 3 | 72 | 85 | 69 |
| | | | Ave. | (79) | (79) | (76) |

TABLE 7

Result of Cardiovascular, Heart Rate (SHR 0, 1, 2, 4 Hours)

| | | | | % Control (from 0 times) | | |
|---|---|---|---|---|---|---|
| Treatment | Route | Dose | N | 1 Hour | 2 Hours | 4 Hours |
| Vehicle | PO | 10 ml/kg | 1 | 87 | 100 | 99 |
| | | | 2 | 116 | 103 | 107 |
| | | | 3 | 108 | 104 | 121 |
| | | | Ave. | 104 | 102 | 109 |
| ACM-EtOH Extract | PO | 1000 mg/kg | 1 | 98 | 93 | 95 |
| | | | 2 | 81 | 100 | 88 |
| | | | 3 | 83 | 78 | 92 |
| | | | Ave. | 87 | 90 | 92 |
| Clonidine | PO | 0.1 mg/kg | 1 | 62 | 97 | 112 |
| | | | 2 | 84 | 87 | 104 |
| | | | 3 | 68 | 86 | 78 |
| | | | Ave. | (71) | 90 | 98 |

SHR with systolic blood pressure of 200±20 mmHg and heart rates of 400±50 mmHg Beats/min were used. Blood pressure was recorded indirectly vial tail cuff at time 0 (before) and 1, 2 and 4 hours after oral administration of vehicle or test substance. A reduction in blood pressure by 10 percent or more ($\geq 10\%$), or decrease in heart rate by 20 percent or more ($\geq 20\%$) at each measurement time point relative to 0 time, shown in parenthesis, is considered significant.

| | |
|---|---|
| Vehicle | 10 ml/kg 0 time 229 mmHg and 403 mmHg beats/minute as 100%. |
| ACM-EtOH Extract | 1000 mg/kg 0 time 223 mmHg and 452 mmHg beats/minute as 100%. |
| Clonidine | 0.1 mg/kg 0 time 228 mmHg and 379 mmHg beats/minute as 100% |

TABLE 8

Result of Cardiovascular, Blood Pressure (SHR 0, 1, 2, 4 Hours) in Rats

| | | | | % Control (from 0 times) | | |
|---|---|---|---|---|---|---|
| Treatment | Route | Dose | N | 1 Hour | 2 Hours | 4 Hours |
| Vehicle | PO | 10 ml/kg | 1 | 94 | 97 | 97 |
| | | | 2 | 88 | 97 | 94 |
| | | | 3 | 94 | 97 | 103 |
| | | | Ave. | 92 | 97 | 98 |
| ACM-EtOH Extract | PO | 300 mg/kg | 1 | 111 | 102 | 103 |
| | | | 2 | 94 | 84 | 100 |
| | | | 3 | 112 | 110 | 112 |
| | | | Ave. | 106 | 99 | 105 |
| Clonidine | PO | 0.1 mg/kg | 1 | 86 | 73 | 81 |
| | | | 2 | 63 | 73 | 90 |
| | | | 3 | 62 | 68 | 80 |
| | | | Ave. | (70) | (71) | (85) |

TABLE 9

Result of Cardiovascular, Heart Rate (SHR 0, 1, 2, 4 Hours)

| | | | | % Control (from 0 times) | | |
|---|---|---|---|---|---|---|
| Treatment | Route | Dose | N | 1 Hour | 2 Hours | 4 Hours |
| Vehicle | PO | 10 ml/kg | 1 | 82 | 85 | 84 |
| | | | 2 | 88 | 115 | 102 |
| | | | 3 | 109 | 111 | 119 |
| | | | Ave. | 93 | 104 | 102 |
| ACM-EtOH Extract | PO | 300 mg/kg | 1 | 97 | 96 | 92 |
| | | | 2 | 105 | 108 | 98 |
| | | | 3 | 85 | 96 | 82 |
| | | | Ave. | 96 | 100 | 91 |
| Clonidine | PO | 0.1 mg/kg | 1 | 77 | 85 | 102 |
| | | | 2 | 78 | 78 | 100 |
| | | | 3 | 62 | 94 | 104 |
| | | | Ave. | (72) | 86 | 102 |

SHR with systolic blood pressure of 200±20 mmHg and heart rates of 400±50 mmHg Beats/min were used. Blood pressure was recorded indirectly vial tail cuff at time 0 (before) and 1, 2 and 4 hours after oral administration of vehicle or test substance. A reduction in blood pressure by 10 percent or more 10%), or decrease in heart rate by 20 percent or more ($\geq 20\%$) at each measurement time point relative to 0 time, shown in parenthesis, is considered significant.

| | |
|---|---|
| Vehicle | 10 ml/kg 0 time 220 mmHg and 410 mmHg beats/minute as 100% |
| ACM-EtOH Extract | 300 mg/kg 0 time 205 mmHg and 446 mmHg beats/minute as 100%. |
| Clonidine | 0.1 mg/kg 0 time 235 mmHg and 417 mmHg beats/minute as 100% |

3. Cholesterol, Serum (Total HDL, total/HDL, Ratio), Diet-Induced (Schurr P E et al., Atherosclerosis Drug Discovery. Plenum, N.Y., pp. 215–229, 1976)

Groups of 5 ICR derived male mice weighing 22±2 g were kept on a high fat diet (g/100 g: coconut oil, 8; cholesterol, 1.0; cholic acid, 0.3; lard 2; standard chow 88.7) for 7 days to induce hypercholesterolemia. Test substance was administered orally on days 5, 6 and 7. After fasting overnight, serum was obtained from each mouse and assayed for total cholesterol (Total), high density lipoprotein (HDL) and percent change in Total/HDL. A decrease of 20 percent or more (≧20%) in serum Total or increase of 20 percent or more (≧20%) in serum HDL or decrease of 40% or more (≧40%) in the Total/HDL ratio relative to vehicle treated control animals is considered significant.

assessing serum total cholesterol (Total) and high density lipoprotein (HDL). Decrease of 20 percent or more (≧20%) in serum Total or increase of 20 percent or more (≧20%) in serum HDL or decrease of 40% or more (≧40%) in the Total/HDL ratio is considered significant.

4. Hepatic Injury, D-Galactosamine (Wrobel J et al., J. Med Chem 41: 1084, 1998)

Groups of 5 Wistar derived male rats weighing 200±20 g were used. Each animal was treated with a single injection of D-galactosamine (500 mg/kg, IP) Test substance was administered orally at 0.5 hour before and 4 hours as well as 8 hours after D-galactosamine administration and animals were sacrificed 24 hours later. Serum alanine aminotransferase (ALT) and aspartate aminotransferase (AST) levels were measured by an optimized UV method with HITACHI

TABLE 10

Result of Cholesterol, (Total/HDL, Total/HDL Ratio), Diet-Induced in Mice

| Treatment | Route | Dose | N | Total Indiv. | % Dce | HDL Indiv. | % Dce | Total/HDL Indiv | % Dce |
|---|---|---|---|---|---|---|---|---|---|
| Vehicle | PO | 10 ml/kg × 3 | 1 | 361 | | 70 | | 5.16 | |
| | | | 2 | 316 | | 82 | | 3.85 | |
| | | | 3 | 379 | | 79 | | 4.80 | |
| | | | 4 | 392 | | 78 | | 5.03 | |
| | | | 5 | 367 | | 86 | | 4.27 | |
| | | | Ave. | 363 | — | 79 | — | 4.59 | — |
| ACM-EtOH Extract | PO | 1000 mg/kg × 3 | 1 | 420 | | 117 | | 3.95 | |
| | | | 2 | 327 | | 115 | | 2.84 | |
| | | | 3 | 332 | | 104 | | 3.19 | |
| | | | 4 | 363 | | 98 | | 3.70 | |
| | | | 5 | 294 | | 117 | | 2.51 | |
| | | | Ave. | 347 | 4 | 110 | (39) | 3.15 | 31 |
| | PO | 300 mg/kg × 3 | 1 | 370 | | 66 | | 5.61 | |
| | | | 2 | 301 | | 65 | | 4.63 | |
| | | | 3 | 217 | | 74 | | 2.93 | |
| | | | 4 | 379 | | 76 | | 4.99 | |
| | | | 5 | 328 | | 98 | | 3.35 | |
| | | | Ave. | 319 | 12 | 76 | −4 | 4.20 | 8 |
| Benzafibrate | PO | 100 mg/kg × 3 | 1 | 230 | | 91 | | 2.53 | |
| | | | 2 | 214 | | 120 | | 1.78 | |
| | | | 3 | 225 | | 133 | | 1.69 | |
| | | | 4 | 231 | | 123 | | 1.88 | |
| | | | 5 | 242 | | 97 | | 2.49 | |
| | | | Ave. | 228 | (37) | 113 | (43) | 2.02 | (56) |

Vehicle, test substance or reference positive compound was administered orally (PO) on days 5, 6 and 7 after being fed a high cholesterol diet. Twenty-four hours after the third dose, the overnight-fasted test animals were sacrificed for automatic analyzer (model 7050). Reduction in ALT or AST activity by 30 percent or more (≧30%), relative to the vehicle treated control animal indicates significant protection.

TABLE 11

Result of Hepatic Injury, Galactosamine in Rats

| Treatment | Route | Dose | N | Serum ALT (X ± SEM) U/L | Dec. % | Serum AST (X ± SEM) U/L | Dec. % |
|---|---|---|---|---|---|---|---|
| Vehicle | PO | 10 mg/kg × 3 | 1 | 816 | | 1628 | |
| | | | 2 | 1044 | | 1716 | |
| | | | 3 | 652 | | 888 | |
| | | | 4 | 656 | | 828 | |
| | | | 5 | 644 | | 956 | |
| | | | X | 762.4 | — | 1203.2 | — |
| | | | SEM | 77.4 | | 193.0 | |

TABLE 11-continued

Result of Hepatic Injury, Galactosamine in Rats

| Treatment | Route | Dose | N | Serum ALT (X ± SEM) U/L | Dec. % | Serum AST (X ± SEM) U/L | Dec. % |
|---|---|---|---|---|---|---|---|
| ACM-EtOH Extract | PO | 1000 mg/kg × 3 | 1 | 364 | | 516 | |
| | | | 2 | 376 | | 532 | |
| | | | 3 | 596 | | 672 | |
| | | | 4 | 452 | | 524 | |
| | | | 5 | 336 | | 356 | |
| | | | X | 424.8 | (44) | 520.0 | (57) |
| | | | SEM | 46.9 | | 50.1 | |
| | | 300 mg/kg × 3 | 1 | 460 | | 852 | |
| | | | 2 | 656 | | 880 | |
| | | | 3 | 640 | | 876 | |
| | | | 4 | 752 | | 1004 | |
| | | | 5 | 536 | | 692 | |
| | | | X | 608.8 | 20 | 860.8 | 28 |
| | | | SEM | 50.6 | | 49.8 | |
| Guanine | PO | 300 mg/kg × 3 | 1 | 508 | | 656 | |
| | | | 2 | 532 | | 912 | |
| | | | 3 | 412 | | 776 | |
| | | | 4 | 436 | | 652 | |
| | | | 5 | 636 | | 1028 | |
| | | | X | 504.8 | (34) | 804.8 | (33) |
| | | | SEM | 39.6 | | 73.4 | |

Test substance and vehicle administered orally at 0.5 hour before and 4, 8 hours after a single dose of galactosamine (500 mg/kg, IP). The rats were sacrificed 24 hours after galactosamine injection and the ALT and AST values were determined. A reduction of $\geq 30\%$ in the ALT and AST relative to the vehicle group is considered significant.

5. Inflammation, Carrageenan (Winter C A et al., Proc Soc Exp Biol Med. 111:544, 1962)

A group of 3 Long Evans derived male or female overnight fasted rats weighing 150±20 g was fasted overnight prior to study. Test substance was administered orally one hour before right hind paw received injection of carrageenan (0.1 ml of 1% suspension intraplantar). Hind paw edema, as a measure of inflammation, was recorded 3 hours after carrageenan administration using a plethysmometer with water cell (25 mm diameter). Reduction of hind paw edema by 30 percent or more ($\geq 30\%$) indicates significant acute anti-inflammatory activity.

TABLE 12

Result of Inflammation, Carrageenan in Rats

| Treatment | Route | Dose | N | Paw Volume (×0.01 ml) R.P. | L.P. | Diff | % Inhibition |
|---|---|---|---|---|---|---|---|
| Vehicle | PO | 10 ml/kg | 1 | 194 | 103 | 91 | |
| | | | 2 | 202 | 108 | 94 | |
| | | | 3 | 199 | 104 | 95 | |
| | | | Ave. | 198 | 105 | 93 | — |
| ACM-EtOH Extract | PO | 1000 mg/kg | 1 | 146 | 101 | 45 | |
| | | | 2 | 147 | 95 | 52 | |
| | | | 3 | 160 | 104 | 56 | |
| | | | Ave. | 151 | 100 | 51 | (45) |
| Aspirin | PO | 150 mg/kg | 1 | 152 | 102 | 50 | |
| | | | 2 | 146 | 102 | 44 | |
| | | | 3 | 163 | 106 | 57 | |
| | | | Ave. | 154 | 103 | 50 | (46) |

TABLE 13

Result of Inflammation, Carrageenan in Rats

| Treatment | Route | Dose | N | Paw Volume (×0.01 ml) | | | % Inhibition |
| --- | --- | --- | --- | --- | --- | --- | --- |
| | | | | R.P. | L.P. | Diff | |
| Vehicle | PO | 10 ml/kg | 1 | 193 | 105 | 88 | |
| | | | 2 | 198 | 107 | 91 | |
| | | | 3 | 199 | 102 | 97 | |
| | | | Ave. | 197 | 105 | 92 | — |
| ACM-EtOH Extract | PO | 300 mg/kg | 1 | 195 | 104 | 91 | |
| | | | 2 | 187 | 103 | 84 | |
| | | | 3 | 196 | 103 | 93 | |
| | | | Ave. | 193 | 103 | 89 | 3 |
| Aspirin | PO | 150 mg/kg | 1 | 146 | 103 | 43 | |
| | | | 2 | 149 | 101 | 48 | |
| | | | 3 | 169 | 104 | 65 | |
| | | | Ave. | 155 | 103 | 52 | (43) |

Vehicle or test substance was administered to overnight fasted rats one hour before right hindpaw (R.P.) injection of carrageenan (0.1 ml of 1% suspension intraplantar); the left hindpaw (L.P.) was not injected. Reduction of hindpaw edema by 30 percent or more ($\geq 30\%$), shown in parenthesis, indicates significant acute anti-inflammatory activity.

6. Tumor, Syngeneic, Melanoma, B16-F0 Cell (Farrugia C A and Groves M J. Anticancer Research 19: 1027–1032, 1999)

Groups of 5 immunocompetent (6–8 weeks old), pathogen-free (SPF) C57BL/6J male mice bred in an animal isolator (IVC racks) under specific pathogen free (SPF) condition were used. Viable B16-F0 murine melanoma cells (ATCC CRL-6322, $1.0 \times 10^5$ in 0.2 ml), syngeneic for C57BL/6J mice, were injected subcutaneously into dorsal side of experimental mice. Treatment begins 24 hours after tumor inoculation and test compound was administered daily by oral gavage for 21 days, or less when overt signs of toxicity are seen. The mice were monitored for body weight, tumor size and survival starting from day 1 to day 22. Moreover, the tested mice were monitored for survival till the end of the study on day 45.

Tumor weight (mg) was estimated according to the formula for a prolate ellipsoid: length (mm)×[width (mm)]²× 0.5, assuming specific gravity to be one and π to be three. Tumor growth in compound treated animals was calculated as T/C (Treatment/Control)×100%; a value of T/C$\leq$42% was considered significant in demonstrating antitumor activity.

The mean survival time of T/C (Treatment/Control) is $\geq$125% is also considered significant in demonstrating antitumor activity.

TABLE 14

Result of Tumor, Syngeneic, Melanoma B16-F0 Cell

| Treatment | Route | Dose | N | Tumor Weight (mg) and % T/C, Mean ± SEM | | | | | |
| --- | --- | --- | --- | --- | --- | --- | --- | --- | --- |
| | | | | Day 1. | T/C(%) | Day 8 | T/C(%) | Day 11 | T/C(%) |
| Vehicle | PO | 10 ml/kg × 21 | 1 | 0 | | 0 | | 60 | |
| | | | 2 | 0 | | 39 | | 298 | |
| | | | 3 | 0 | | 0 | | 49 | |
| | | | 4 | 0 | | 54 | | 541 | |
| | | | 5 | 0 | | 21 | | 117 | |
| | | | | 0 | 100 | 23 ± 11 | 100 | 213 ± 93 | 100 |
| ACM-EtOH Extract | PO | 1000 mg/kg × 21 | 1 | 0 | | 0 | | 0 | |
| | | | 2 | 0 | | 0 | | 0 | |
| | | | 3 | 0 | | 0 | | 0 | |
| | | | 4 | 0 | | 0 | | 14 | |
| | | | 5 | 0 | | 0 | | 32 | |
| | | | | 0 | 100 | 0 ± 0 | 0* | 9 ± 6 | 4* |
| Mitomycin | IP | 2 mg/kg × 6 | 1 | 0 | | 0 | | 0 | |
| | | | 2 | 0 | | 0 | | 64 | |
| | | | 3 | 0 | | 0 | | 0 | |
| | | | 4 | 0 | | 0 | | 68 | |
| | | | 5 | 0 | | 0 | | 41 | |
| | | | | 0 | 100 | 0 ± 0 | 0* | 34 ± 15 | 16* |

TABLE 15

Result of Tumor, Syngeneic, Melanoma B16-F0 Cell

| Treatment | Route | Dose | N | Day 15 | T/C(%) | Day 18 | T/C(%) | Day 22 | T/C(%) |
|---|---|---|---|---|---|---|---|---|---|
| Vehicle | PO | 10 ml/kg × 21 | 1 | 211 | | 746 | | 2054 | |
| | | | 2 | 657 | | 1597 | | 2870 | |
| | | | 3 | 216 | | 669 | | 1419 | |
| | | | 4 | 835 | | 2455 | | 3688 | |
| | | | 5 | 240 | | 726 | | 1682 | |
| | | | | 432 ± 131 | 100 | 1239 ± 349 | 100 | 2343 ± 416 | 100 |
| ACM-EtOH Extract | PO | 1000 mg/kg × 21 | 1 | 49 | | 280 | | 913 | |
| | | | 2 | 62 | | 630 | | 1545 | |
| | | | 3 | 388 | | 1079 | | 2560 | |
| | | | 4 | 148 | | 435 | | 1514 | |
| | | | 5 | 229 | | 535 | | 1637 | |
| | | | | 175 ± 62 | 41* | 592 ± 135 | 48 | 1634 ± 265 | 70 |
| Mitomycin | IP | 2 mg/kg × 6 | 1 | 36 | | 256 | | 437 | |
| | | | 2 | 136 | | 849 | | 1248 | |
| | | | 3 | 0 | | 0 | | 0 | |
| | | | 4 | 213 | | 525 | | 663 | |
| | | | 5 | 207 | | 327 | | Died | |
| | | | | 119 ± 44 | 27* | 391 ± 142 | 32* | 587 ± 260 | 25* |

Vehicle and test substance were administered to test animals every day at 24 hours after tumor cells implantation for a total of 21 doses. Concurrently, the reference compound, mitomycin, was administered IP twice a week for a total of 6 doses. Tumor size was measured and recorded twice a week for a period of 22 days. Tumor growth inhibition was calculated as T/C (treatment/control)×100. A T/C value of ≦42% was considered significant in demonstrating antitumor activity.

Vehicle and test substance were administered to test animals every day at 24 hours after tumor cells implantation for a total of 21 doses. Concurrently, the reference compound. Tumor size was administered IP twice a week for a total of 6 doses. Tumor size was measured and recorded twice a week for a period of 22 days. The Student's t test was used to determine the siginifcant difference in the change of body weight between test compound and vehicle control group.

TABLE 16

Result of Tumor, Syngeneic, Melanoma B16-F0 Cell

| Treatment | Route | Dose | N | Day 1 | Day 8 | Day 11 | Day 15 | Day 18 | Day 22 |
|---|---|---|---|---|---|---|---|---|---|
| Vehicle | PO | 10 ml/kg × 21 | 1 | 21 | 20 | 20 | 21 | 22 | 25 |
| | | | 2 | 22 | 22 | 21 | 22 | 26 | 30 |
| | | | 3 | 21 | 21 | 20 | 20 | 22 | 21 |
| | | | 4 | 21 | 20 | 20 | 20 | 21 | 24 |
| | | | 5 | 22 | 21 | 20 | 19 | 20 | 23 |
| | | | | 21.4 ± 0.2 | 20.8 ± 0.4 | 20.2 ± 0.2 | 20.4 ± 0.5 | 22.2 ± 1.0 | 24.6 ± 1.5 |
| ACM-EtOH Extract | PO | 1000 mg/kg × 21 | 1 | 20 | 21 | 21 | 22 | 22 | 23 |
| | | | 2 | 20 | 19 | 19 | 21 | 22 | 24 |
| | | | 3 | 20 | 18 | 18 | 19 | 21 | 26 |
| | | | 4 | 21 | 20 | 19 | 21 | 20 | 21 |
| | | | 5 | 20 | 20 | 21 | 22 | 23 | 25 |
| | | | | 20.2 ± 0.2 | 19.6 ± 0.5 | 19.6 ± 0.6 | 21.0 ± 0.5 | 21.6 ± 0.5 | 23.8 ± 0.9 |
| Mitomycin | IP | 2 mg/kg × 6 | 1 | 25 | 25 | 26 | 25 | 24 | 27 |
| | | | 2 | 22 | 22 | 22 | 25 | 27 | 30 |
| | | | 3 | 19 | 21 | 21 | 21 | 22 | 21 |
| | | | 4 | 22 | 22 | 22 | 24 | 26 | 27 |
| | | | 5 | 19 | 20 | 19 | 20 | 21 | Died |
| | | | | 21.4 ± 1.1 | 22.2 ± 0.8 | 22.0 ± 1.1 | 23.0 ± 1.0 | 24.0 ± 1.1 | 26.3 ± 1.9 |

TABLE 17

Result of Tumor, Syngeneic, Melanoma B16-F0 Cell

| Treatment | Route | Dose | N | Days of Post-treatment | T/C (%) |
|---|---|---|---|---|---|
| Vehicle | PO | 10 ml/kg × 21 | 1 | 23 | |
| | | | 2 | 28 | |
| | | | 3 | 30 | |
| | | | 4 | 28 | |
| | | | 5 | 27 | |
| | | | | 27.2 ± 1.2 | 100 |
| ACM-EtOH Extract | PO | 1000 mg/kg × 21 | 1 | 44 | |
| | | | 2 | 31 | |
| | | | 3 | 25 | |
| | | | 4 | 42 | |
| | | | 5 | 32 | |
| | | | | 34.8 ± 3.6 | 128* |
| Mitomycin | IP | 2 mg/kg × 6 | 1 | 45[a] | |
| | | | 2 | 28 | |
| | | | 3 | 45[a] | |
| | | | 4 | 30 | |
| | | | 5 | 22 | |
| | | | | 34.0 ± 4.7 | 125* | a: The animal did not die through day 45 and the survival day was served as 45 days.

The treated mice were monitored for survival through the end of the study on day 45 od the day when test animal died. The mean survival time of T/C (Treatment/Control)≧125% is also considered significant in demonstrating anti-tumor activity.

Discussion:

ACM-EtOH Extract, administered orally (PO), in accordance with in-house established criteria, caused significant activities in the following mouse and rat assays:

Central cholinergic agonism at 1000 mg/kg in rats; a minimum and non-significant agonism was seen a 300 mg/kg; no significant agonism or antagonism on peripheral cholinergic nerve was seen at 1000 mg/kg (Table 5)

Decrease in systolic blood pressure (16%, 12% and 20% at respective 1, 2 and 4 hours observation time points vs. 100% with 0 time) and associated moderate but non-significant decrease in heart rate at 1000 mg/kg in spontaneously hypertensive (SH) rats (Tables 6 and 7); dose of 300 mg/kg did not cause significant changes in systolic blood pressure nor the heart rate (Tables 8 and 9)

Increase in high density lipoprotein (HDL, 39% over vehicle control) at 1000 mg/kg in diet-induced mice (Table 10); the associate total cholesterol (Total) did not change significantly, while the HDL/total ratio was decreased to near significant 31%; dose of 300 mg/kg did not cause significant changes in Total, HDL and HDL/Total ratio (Table 10).

Hepatoprotection (44% decrease in ALT and 57% decrease in AST vs. vehicle control) from galactosamine induced hepatic injury in rats at 1000 mg/kg×3; moderate decrease of 20% in ALT and of 28% in AST at 300 mg/kg×3 was seen (Table 11)

Anti-inflammation (45% inhibition vs. vehicle control) versus carrageenan-induced paw edema in rats at 1000 mg/kg (Table 12); the lower level of 300 mg/kg did not demonstrate significant activity (3% inhibition vs. vehicle, Table 13)

Anti-tumor activity in syngeneic melanoma B16-F0 cell for C57BL/6J mice on day 8, 11 and 15 (Tables 14 and 15) as well as prolongation in animal survival time at 1000 mg/kg (Table 17); animal body weight did not change significantly (Table 16).

Tests for ACM, ACM-ETOH Extract and Compound 3 of the Invention Nine groups of ICR derived male mice (weighing 22±2 g) of 5 each were used.

Each animals was challenged with a single dose of carbon tetrachloride ($CCl_4$, 0.1 ml/kg in 50% olive oil, PO). The test substance of ACM at doses 300 and 1000 mg/kg or compound 3 of the invention at doses 30, 100 and 300 mg/kg were administered orally at 30 minutes before and 4, 8 hours after $CCl_4$ challenge; whereas ACM-ETOH Extract at 300 and 1000 mg/kg administered orally was pretreated one day (twice a day) and 30 minutes before and 4, 8 hours after carbon tetrachloride The animals were sacrificed 24 hours after $CCl_4$. Alanine aminotransferase (ALT) and Aspartate aminotransferase (AST) levels were measured by optimized UV method using a HITACHI automatic analyzer (model 7050). A reduction of ALT or AST levels by 30 percent or greater (≧30%), relative to the vehicle group, indicating significant protection from hepatic injury.

Results

TABLE 18

Assay Hepatic Injury, Carbon Tetrachloride, in Mice

| Treatment | Route | Dose | N | ALT U/L | ALT Dec. % | AST U/L | AST Dec. % |
|---|---|---|---|---|---|---|---|
| Vehicle (2% Tween 80) | PO | 10 ml/kg × 3 | 1 | 3936 | | 2056 | |
| | | | 2 | 3456 | | 1856 | |
| | | | 3 | 3712 | | 1528 | |
| | | | 4 | 2560 | | 1328 | |
| | | | 5 | 2968 | | 1696 | |
| | | | X | 3326 | 0 | 1693 | 0 |
| | | | SEM | 250 | | 126 | |
| ACM | PO | 1000 mg/kg × 3 | 1 | 1440 | | 888 | |
| | | | 2 | 2720 | | 1520 | |
| | | | 3 | 2272 | | 1328 | |
| | | | 4 | 1272 | | 792 | |
| | | | 5 | 1320 | | 880 | |
| | | | X | 180.5 | (46) | 1082 | (36) |
| | | | SEM | 292 | | 144 | |
| | | 300 mg/kg × 3 | 1 | 2336 | | 1256 | |
| | | | 2 | 1552 | | 1072 | |
| | | | 3 | 3720 | | 1512 | |

TABLE 18-continued

Assay Hepatic Injury, Carbon Tetrachloride, in Mice

| Treatment | Route | Dose | N | ALT U/L | ALT Dec. % | AST U/L | AST Dec. % |
|---|---|---|---|---|---|---|---|
| | | | 4 | 3816 | | 2336 | |
| | | | 5 | 3952 | | 2792 | |
| | | | X | 3075 | 8 | 1794 | −6 |
| | | | SEM | 480 | | 330 | |
| ACM-EtOH Extract | PO | 1000 mg/kg × 5 | 1 | 1936 | | 1232 | |
| | | | 2 | 1528 | | 768 | |
| | | | 3 | 1896 | | 1136 | |
| | | | 4 | 2752 | | 1656 | |
| | | | 5 | 2472 | | 1592 | |
| | | | X | 2117 | (36) | 1277 | 25 |
| | | | SEM | 219 | | 162 | |
| | | 300 mg/kg × 5 | 1 | 1656 | | 976 | |
| | | | 2 | 3536 | | 1712 | |
| | | | 3 | 2328 | | 1808 | |
| | | | 4 | 1736 | | 1416 | |
| | | | 5 | 1792 | | 888 | |
| | | | X | 2210 | (34) | 1360 | 20 |
| | | | SEM | 352 | | 187 | |
| Compound 3 | PO | 300 mg/kg × 3 | 1 | 1368 | | 776 | |
| | | | 2 | 1576 | | 896 | |
| | | | 3 | 1440 | | 896 | |
| | | | 4 | 2728 | | 1352 | |
| | | | 5 | 2720 | | 1728 | |
| | | | X | 1966 | (41) | 1130 | (33) |
| | | | SEM | 311 | | 179 | |
| | | 100 mg/kg × 3 | 1 | 3200 | | 2256 | |
| | | | 2 | 4576 | | 2976 | |
| | | | 3 | 2512 | | 1536 | |
| | | | 4 | 2728 | | 1552 | |
| | | | 5 | 3696 | | 1600 | |
| | | | X | 3342 | 0 | 1984 | −17 |
| | | | SEM | 370 | | 282 | |
| | | 30 mg/kg × 3 | 1 | 4296 | | 2136 | |
| | | | 2 | 3696 | | 2288 | |
| | | | 3 | 2152 | | 1096 | |
| | | | 4 | 2400 | | 1792 | |
| | | | 5 | 4256 | | 2496 | |
| | | | X | 3360 | −1 | 1962 | −16 |
| | | | SEM | 457 | | 245 | |
| Silymarin | PO | 100 mg/kg × 3 | 1 | 2856 | | 1296 | |
| | | | 2 | 1832 | | 1152 | |
| | | | 3 | 1296 | | 952 | |
| | | | 4 | 2792 | | 1072 | |
| | | | 5 | 2728 | | 1336 | |
| | | | X | 2301 | (31) | 1162 | (31) |
| | | | SEM | 3136 | | 71 | |

Discussion:

ACM, ACM-EtOH Extract and compound 3 of the invention were evaluated for possible protective activity from hepatic injury induced by carbon tetrachloride in ICR mice. The test substance of ACM at doses 300 and 1000 mg/kg and compound 3 of the invention at doses 30, 100 and 300 mg/kg were administered orally to test animals 0.5 hour before and 4, 8 hours after $CCl_4$ challenge. For ACM-EtOH Extract at 300 and 1000 mg/kg, 2 times (b.i.d.) of treatment (9:00 AM and 16:00 PM) were done 1 day before $CCl_4$ and followed 0.5 hr before and 4, 8 hours after $CCl_4$ challenge (5 dosing in total). The degree of hepatic injury was determined by increase in serum alanine aminotransferase (ALT) and aspartate aminotransferase (AST) levels relative to the vehicle treated animals. ACM at 1000 mg/kg×3 and compound 3 of the invention at 300 mg/kg×3 caused a significant reduction of ALT (46% and 41%) and AST (36% and 33%) relative to the vehicle treated animals. Simultaneously, ACM-EtOH Extract at 300 and 1000 mg/kg×5 also caused significant reduction in ALT (36% and 34%) and AST (25% and 20%).

Concurrently tested silymarin (100 mg/kg×3, IP) showed significantly reduction of ALT (31%) and AST (31%) relative to the vehicle treated group.

It is concluded that ACM, ACM-EtOH Extract and compound 3 of the invention possess the ability of significant hepatoprotectant activity in a mouse $CCl_4$ model.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A compound having the formula

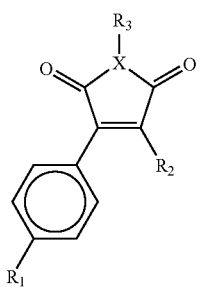

wherein X is N;
R$_1$ is C$_{2-10}$ alkenyloxy or C$_{2-10}$ alkynyloxy;
R$_2$ is C$_{1-10}$ alkyl, C$_{2-10}$ alkenyl or C$_{2-10}$ alkynyl; and
R$_3$ is H or hydroxyl.

2. The compound of claim 1, wherein
R$_1$ is C$_{2-6}$ alkenyloxy or C$_{2-6}$ alkynyloxy.

3. The compound of claim 2, wherein
C$_{2-6}$ alkenyloxy is substituted with C$_{1-6}$ alkyl.

4. The compound of claim 1, wherein
R$_2$ is isobutyl.

5. The compound of claim 1, which is
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-l-ol-2,5-dione,
3R*,4S*-1 -hydroxy-3-isobutyl-4-[4-(3-methyl-2-butenyloxy)phenyl]pyrrolidine-2,5-dione, or
3R*,4R*-1-hydroxy-3-isobutyl-4-[4-(3-methyl-2-butenyloxy)phenyl]pyrrolidine-2,5-dione.

6. A composition comprising a compound having the formula

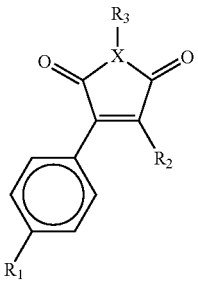

wherein X is N;
R$_1$ is C$_{2-10}$ alkenyloxy, or C$_{2-10}$ alkynyloxy;
R$_2$ is C$_{1-10}$ alkyl, C$_{2-10}$ alkenyl or C$_{2-10}$ alkynyl; and R$_3$ is H or hydroxyl; and
a pharmaceutically acceptable excipient.

7. The composition of claim 6, wherein the compound is
3-isobutyl-4-[4-(3-methyl-2-butenyloxy)phenyl]-1H-pyrrol-2,5 -dione,
3-isobutyl-4-[4-(3-methyl-2-butenyloxy)phenyl]-1H-pyrrol-l-ol-2,5 -dione,
3R*,4S*-1-hydroxy-3-isobutyl-4-[4-(3-methyl-2-butenyloxy)phenyl]pyrrolidine-2,5-dione, or
3R*,4R*-1--hydroxy-3-isobutyl-4-[4-(3-methyl-2-butenyloxy)phenyl]pyrrolidine-2,5-dione.

8. The composition of claim 7, wherein the compound is 3-isobutyl-4-[4-(3-methyl-2-butenyloxy)phenyl]-1H-pyrrol-2,5-dione or 3-isobutyl-4-[4-(3-methyl-2-butenyloxy)phenyl]-1H-pyrrol-l-ol-2,5 -dione.

9. The composition of claim 6, which decreases systolic blood pressure or increases high density lipoprotein.

10. The composition of claim 6, which has central cholinergic agonism, hepatoprotection, anti-inflammation or anti-tumor activity wherein anti-tumor activity is exhibited against a tumor from cells or tissues selected from a group consisting of liver, intestine, bone, blood, lymph and breast.

11. The composition of claim 10, wherein the anti-tumor activity is exhibited against a tumor from cells or tissues selected from a group consisting of liver, intestine, bone, blood, lymph and breast.

12. The composition according to claim 6, further comprising:
a compound having the formula

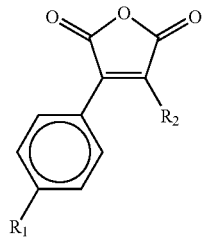

wherein
R$_1$ is C$_{2-10}$ alkenyloxy or C$_{2-10}$ alkynyloxy; and
R$_2$ is H, C$_{1-10}$ alkyl, C$_{2-10}$ alkenyl or C$_{2-10}$ alkynyl.

* * * * *